US009387234B2

(12) United States Patent
Itescu

(10) Patent No.: US 9,387,234 B2
(45) Date of Patent: *Jul. 12, 2016

(54) USE OF SDF-1 TO IMPROVE ISCHEMIC MYOCARDIAL FUNCTION

(71) Applicant: Silviu Itescu, New York, NY (US)

(72) Inventor: Silviu Itescu, New York, NY (US)

(73) Assignee: THE TRUSTEES OF COLUMBIA UNIVERSITY IN THE CITY OF NEW YORK, New York, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/938,608

(22) Filed: Jul. 10, 2013

(65) Prior Publication Data

US 2015/0150943 A1    Jun. 4, 2015

Related U.S. Application Data

(63) Continuation of application No. 12/657,264, filed on Jan. 15, 2010, now Pat. No. 8,486,416, which is a continuation of application No. 11/234,879, filed on Sep. 22, 2005, now Pat. No. 7,662,392, which is a continuation of application No. 10/220,554, filed as application No. PCT/US01/18399 on Jun. 5, 2001, now abandoned, which is a continuation-in-part of application No. 09/587,441, filed on Jun. 5, 2000, now abandoned.

(51) Int. Cl.
*A61K 38/19* (2006.01)
*C07K 14/52* (2006.01)
*C07K 16/24* (2006.01)
*C07K 16/28* (2006.01)
*C12N 5/071* (2010.01)
*A61K 35/44* (2015.01)
*A61K 39/00* (2006.01)

(52) U.S. Cl.
CPC .............. *A61K 38/195* (2013.01); *A61K 35/44* (2013.01); *A61K 38/193* (2013.01); *C07K 16/24* (2013.01); *C07K 16/2866* (2013.01); *C12N 5/0692* (2013.01); *A61K 2039/505* (2013.01); *C07K 14/52* (2013.01); *C12N 2501/21* (2013.01)

(58) Field of Classification Search
None
See application file for complete search history.

(56) References Cited

U.S. PATENT DOCUMENTS

| 5,008,284 A * | 4/1991 | Grover et al. ................. 514/423 |
| 5,061,620 A | 10/1991 | Tsukamoto et al. |
| 5,552,381 A | 9/1996 | Atkinson |
| 5,599,703 A | 2/1997 | Davis et al. |
| 5,880,090 A | 3/1999 | Hammond et al. |
| 5,980,887 A | 11/1999 | Isner et al. |
| 6,106,830 A | 8/2000 | Li |
| 6,288,103 B1 | 9/2001 | Faull et al. |
| 7,662,392 B2 * | 2/2010 | Itescu .................... 424/198.1 |
| 8,486,416 B2 * | 7/2013 | Itescu .................... 424/198.1 |
| 8,663,652 B2 * | 3/2014 | Itescu .................... 424/198.1 |
| 2002/0094327 A1 | 7/2002 | Petersen |
| 2002/0107195 A1 * | 8/2002 | Gupta .......................... 514/12 |
| 2002/0115081 A1 | 8/2002 | Lee et al. |
| 2003/0054418 A1 | 3/2003 | Bodnar et al. |
| 2003/0054973 A1 | 3/2003 | Anversa |
| 2003/0171294 A1 | 9/2003 | Hung et al. |
| 2003/0199464 A1 | 10/2003 | Itescu |
| 2004/0247564 A1 | 12/2004 | Itescu |
| 2005/0233992 A1 | 10/2005 | Itescu |
| 2006/0051334 A1 | 3/2006 | Kornowski |
| 2006/0057722 A1 | 3/2006 | Kornowski |
| 2006/0111290 A1 | 5/2006 | Itescu |
| 2007/0172467 A1 | 7/2007 | Itescu |
| 2008/0057069 A1 | 3/2008 | Itescu |
| 2009/0142296 A1 | 6/2009 | Itescu |

FOREIGN PATENT DOCUMENTS

| EP | 0897980 | 2/1999 |
| WO | WO 98/19712 A | 5/1998 |
| WO | WO 98/54210 | 12/1998 |
| WO | WO 99/37751 | 7/1999 |
| WO | WO 99/37779 | 7/1999 |
| WO | WO 99/43839 | 9/1999 |
| WO | WO 99/45775 A | 9/1999 |
| WO | WO 99/65507 | 12/1999 |
| WO | WO 00/57922 | 5/2000 |
| WO | WO 02/036078 | 10/2001 |
| WO | WO 01/94420 | 12/2001 |
| WO | WO 02/16416 | 2/2002 |
| WO | WO 03/047616 | 6/2003 |
| WO | WO 03/090512 | 11/2003 |

OTHER PUBLICATIONS

Arai, A. et al. (1997), "Murine Cardiac Progenitor Cells Require Visceral Embryonic Endoderm and Primitive Streak for . . . " Developmental Dynamics, 210:344-353.
Asahara, Takayuki et al. (1997) Science 275, pp. 964-967.
Asahara, Takayuki et al. (1999) "VEGF Contributes to Postnatal Neovascularization by Mobilizing Bone Marrow-Derived Endothelial . . . " The EMBO Journal 18, pp. 3964-3972.
Asahara, Takayuki et al. (1999) Circulation Research 85, pp. 221-228.
Askari, Arman T. et al. (2003), "Effect of Stromal-Cell-Derived Factor 1 on Stem-Cell Homing and Tissue Regeneration in Ischaemic Cardiomyopathy" The Lancet 362, pp. 697-703.

(Continued)

*Primary Examiner* — Bridget E Bunner
(74) *Attorney, Agent, or Firm* — John P. White; Cooper & Dunham LLP

(57) ABSTRACT

A method is provided for increasing trafficking of endothelial progenitor cells to an ischemic myocardium in a subject's heart comprising administering to the subject's heart an amount of Stromal-Derived Factor-1 (SDF-1).

8 Claims, 50 Drawing Sheets

(56) References Cited

OTHER PUBLICATIONS

Behl, C. (2000), "Apoptosis and Alzheimer's Disease" J Neural Transm 107, pp. 1325-1344.
Beltrami, Antonio P. et al. (2001) "Evidence That Human Cardiac Myocytes Divide After Myocardial Infarction" New England J. Med 344, pp. 1750-1757.
Bhattachaya, et al. (2000) J. Vasc. Surgery 32, pp. 116-123.
Bonaros et al. (2008), "CCR3- and CXCR4-mediated Interactions Regulate Migration of CD34+ Human Bone Marrow Progenitors . . . " J. Thor. Cardio. Surg. 136(4), pp. 1044-1053.
Canard, Robin E. et al. (1994) The Cytokine FactsBook, Academic Press.
Canbay, Ali et al. (2005), "Apoptosis and Fibrosis in Non-Alcoholic Fatty Liver Disease" Turk J. Gastroenterol 16(1), pp. 1-6.
Chavakis, E. (2006) "IL-8: A New Player in the Homing of Endothelial Progenitor Cells to Ischemic Myocardium," J. Mol. Cell. Cardiol. 40, pp. 442-445.
Choi, K. et al. (1998) Development 125, pp. 725-732.
Dale, et al. (1993) Blood 81, pp. 2496-2502.
De Revel, et al. (1994) Blood 83(12), pp. 3795-3799.
Elefanty, A.G. et al. (1997) Blood 90, pp. 362-367.
Feucht, M. (1997) Am. J. Path. 151(5), pp. 1407-1416.
Futamatsu, H. et al. (2003) Cardiovascular Research 59(1), pp. 95-105.
Gupta, S. et al. (2002) Biochem. Biophys. Acta. 1589(3), pp. 247-260.
Hattori, Koichi et al. (2001), "Plasma Elevation of Stromal Cell-derived Factor-1 Induces Mobilization of Mature and Immature Hematopoietic . . . " Blood 97(11), pp. 3354-3360.
Itescu et al. (2003) "Myocardial neovascularization by adult bone marrow-derived angioblasts: strategies for improvement of cardiomyocyte . . . " Heart Failure Rev 8: 253-258.
Itescu et al. (2003) "New directions in strategies using cell therapy for heart disease" J Mol Med 81: 288-296.
Jaffredo, T. et al. (1998) Development 125, pp. 4575-4583.
Junn et al. (2000) "Vitmain D3 Up-Regulated Protein 1 Mediates Oxidatvie Stress Via Suppressing the Thioredoxin Function" J. Immunol 164(12), p. 6287-6295.
Kajstura, Jan et al. (1998) "Myocyte Proliferation in End-Stage Cardiac Failure in Humans" Proc. Natl. Acad. Sci. USA 95, pp. 8801-8805.
Kalka, Christoph et al. (2000) "Transplantation of Ex Vivo Expanded Endothelial Progenitor Cells for Therapeutic Neovascularization" PNAA 97, pp. 3422-3427.
Kawamoto, Atsuhiko et al. (2001) "Therapeutic Potential of Ex Vivo Expanded Endothelial Progenitor Cells for Myocardial Ischemia" Circulation 103, pp. 634-637.
Kennedy, M. et al. (1997) Nature 386, pp. 488-493.
Kocher, A.A. et al. (2001) "Neovascularization of Ischemic Myocardium by Human Bone-Marrow-Derived Angioblasts Prevents Cardiomyocyte . . . " Nature Med. 7, pp. 430-436.
Kocher, et al. (2006) "Myocardial Homing and Neovascularization by Human Bone Marrow Angioblasts is Regulated by IL-8/Gro CXC . . . " J. Mol. Cell. Cardiol. 40, pp. 455-464.
Labastie, M.-C. et al. (1998) Blood 92, pp. 3624-3635.
Lataillade, Jean-Jacques et al. (2000), "Chemokine SDF-1 Enhances Circulating CD34+ Cell Proliferation in Synergy with Cytokines: Possible Role . . . " Blood 95(3), pp. 756-768.
Lee et al. (1991) J. Biol. Chem. 266(24) 16188-16192.
Lefer, et al. (1991) "Cardioprotective and Endothelial Protective Effects of [Ala-IL8]77 in a Rabbit Model of Myocardial Ischaemia . . . " Br. J. Pharmacol. 103, pp. 1152-1159.
Lin, Y. et al. (2000) J. Clin. Invest. 105, pp. 71-77.
Mohle et al, (1998) "The Chemokine Receptor CXCR-4 Is Expressed on CD34+ Hematopoietic Progenitors and Leukemic Cells and Mediates . . . " Blood 91(12), pp. 4523-4530.
Molineaux, et al. (1990) Blood 76, pp. 2153-2158.
Moore, M.A.S. et al. (2001), "Mobilization of Endothelial and Hematopoietic Stem and Progenitor Cells by Adenovector-Mediated Elevation . . . " Annals NY Acad Sci 938, pp. 36-47.
Murohara, Toyoaki et al. (2000) "Transplanted Cord Blood-Derived Endothelial Precursor Cells Augment Postnatal . . . " J. Clinical Investigation 105, pp. 1527-1536.
Nagasawa, Takashi (2001), "Role of Chemokine SDF-1/PBSF and Its Receptor CXCR4 in Blood Vessel Development" Ann NY Acad Sci 947, pp. 112-116.
Noishiki et al. (1999) "Angiogenic growth factor release system for in vivo tissue engineering: a trial of bone marrow transplantation . . . " J Artif Organs 2: 85-91.
Okuno et al. (2000) Lab. Invest. 80(3), pp. 433-440.
Orlic et al. (2001) "Mobilized bone marrow cells repair the infarcted heart, improving function and survival" Proc Natl Acad Aci USA 98(18):10344-10349.
Peichev, M. et al. (2000) Blood 95, 952-8.
Peled, Amnon et al. (2000), "The Chemokine SDF-1 Activates the Integrins LFA-1, VLA-4, and VLA-5 on Immature Human CD34+ Cells: Role in . . . " Blood 95(11), pp. 3289-3296.
Petit, Isabelle et al. (2007), "The SDF-1-CXCR4 Signaling Pathway: A Molecular Hub Modulating Neo-Angiogenesis" Trends in Immunology 28(7), pp. 299-307.
Placentini, L. et al. (2000), J. Mol. Cell. Cardiol. 32(4), pp. 565-567.
Rempel, Sandra A. et al. (2000), "Identification and Localization of the Cytokine SDF1 and Its Receptor, CXC Chemokine . . . " Clinical Cancer Research 6, pp. 102-111.
Salcedo, Rosalba et al. (1999), "Vascular Endothelial Growth Factor and Basic Fibroblast Growth Factor Induce . . . " The American Journal of Pathology 154(4), pp. 1125-1135.
Shi, Q. et al. (1998) Blood 92, pp. 362-367.
Stenhoff, J. et al. (2004), Biochem. Biophys. Res. Comm. 319(3), pp. 871-878.
Tachibana, Kazunobu et al. (1998), "The chemokine Receptor CXCR4 is Essential for Vascularization of the Gastrointestinal Tract" Nature 393(11), pp. 591-594.
Takahashi, T. et al. (1999) Nat. Med. 5, pp. 434-438.
Tews, D.S. (2002), "Apoptosis and Muscle Fibre Loss in Neuromuscular Disorders" Neuromuscular Disorders 12, pp. 613-622.
Tavian, M. et al. (1996) Blood 87, pp. 67-72.
Tsai, F.Y. et al. (1994) Nature 371, pp. 221-225.
UniprotKB/Swiss-Prot P10145 (IL_8HUMAN), www.uniprot/P10145. Last Modified May 26, 2009. Version 120.
Wang, L. (2000) "ACE Inhibitors and Beta Blockers Equally Attenuate Ischemia-Induced Reduction in Ventricular Fibrillation Threshold," Exp. Clin. Cardiol. 5(2):82-86.
Woo, David (1995) "Apoptosis and Loss of Renal Tissue in Polycystic Kidney Diseases" New England Journal of Medicine 333(1), pp. 18-25.
Yamaguchi, Jun-ichi et al. (2003), "Stromal Cell-Derived Factor-1 Effects on Ex Vivo Expanded Endothelial Progenitor . . . " Circulation 107, pp. 1322-1328.
Yin et al. (1997) "AC 133, A novel marker for human hematopoietic stem and progenitor cells" Blood 90(12):5002-5012.
Yu, Lan et al. (2006), "Identification and Expression of Novel Isoforms of Human Stromal Cell-Derived Factor 1" Gene 374, pp. 174-179.
Zhou, Y et al. (2000), "Mouse Peroxiredoxin V Is a Thioredoxin Peroxidase That Inhibits p53-Induced . . . " Biochemical and Biophysical Research Communications 268:1921-1927.
Supplementary Partial European Search Report issued on Oct. 25, 2004 in connection with E.P. Application No. 01942041.3.
European Search Report issued on Apr. 26, 2004 in connection with E.P. 01942041.3.
European Search Report issued on Aug. 28, 2008 in connection with European Patent Application No. EP 03724217.9.
International Search Report issued on Oct. 18, 2001 in connection with International Application No. PCT/US01/18399.
International Search Report issued on Aug. 24, 2004 in connection with International Application No. PCT/US03/12768.
Oct. 6, 2004 Office Action issued in connection with U.S. Appl. No. 10/128,738.

(56) References Cited

OTHER PUBLICATIONS

Apr. 8, 2005 Office Action issued in connection with U.S. Appl. No. 10/128,738.
Jul. 29, 2005 Office Action issued in connection with U.S. Appl. No. 10/128,738.
Mar. 27, 2006 Office Action issued in connection with U.S. Appl. No. 10/220,554.
May 12, 2006 Official Action issued in connection with Mexican Patent Application No. PA/a/2002/012067.
Jun. 27, 2006 Office Communication issued in connection with U.S. Appl. No. 10/693,480.
Oct. 18, 2006 Office Action issued in connection with U.S. Appl. No. 10/693,480.
Mar. 27, 2007 Office Action issued in connection with U.S. Appl. No. 10/693,480.
Aug. 8, 2007 Office Action issued in connection with U.S. Appl. No. 10/693,480.
Aug. 14, 2007 Office Action issued in connection with U.S. Appl. No. 10/512,518.
Nov. 28, 2007 Office Action issued in connection with U.S. Appl. No. 11/648,769.
Jan. 22, 2008 Office Action issued in connection with U.S. Appl. No. 11/234,879.
Mar. 20, 2008 Examination Report in connection with European Patent Application No. EP 01942041.3.
May 9, 2008 Office Action issued in connection with U.S. Appl. No. 10/693,480.
May 30, 2008 Office Action issued in connection with U.S. Appl. No. 10/512,518.
Jun. 19, 2008 Official Action issued in connection with Mexican Patent Application No. PA/a/2002/012067.
Sep. 26, 2008 Office Action issued in connection with U.S. Appl. No. 11/648,769.
Nov. 20, 2008 Final Office Action issued in connection with U.S. Appl. No. 11/234,879.
Dec. 31, 2008 Office Action issued in connection with U.S. Appl. No. 11/894,555.
Feb. 3, 2009 Final Office Action issued in connection with U.S. Appl. No. 10/693,480.
Feb. 12, 2009 Office Action issued in connection with U.S. Appl. No. 11/894,555.
Mar. 3, 2009 Official Action issued in connection with Japanese Patent Application No. 2003-587162.
Mar. 10, 2009 Office Action issued in connection with U.S. Appl. No. 10/512,518.
Mar. 12, 2009 Official Action issued in connection with European Patent Application No. EP03724217.9.
Mar. 13, 2009 Office Action issued in connection with U.S. Appl. No. 11/648,769.
Jun. 12, 2009 Office Action issued in connection with U.S. Appl. No. 11/894,581.
May 5, 2009 Official Action issued in connection with Canadian Patent Application No. 2,412,436.
Jul. 9, 2009 Notice of Allowance issued in connection with U.S. Appl. No. 11/234,879.
Mar. 27, 2002 Office Action issued in connection with U.S. Appl. No. 09/587,441.
Jan. 2, 2002 Office Action issued in connection with U.S. Appl. No. 09/587,441.
Sep. 19, 2001 Office Action issued in connection with U.S. Appl. No. 09/587,441.
Janeway et al. (1997) "Immunobiology: The Immune System in Health and Disease" NY: Current Biology Limited 1, pp. 11-12.
Khachigian, LM (2000) "Catalytic DNAs as Potential Therapeutic Agents and Sequence-Specific Molecular Tools to Dissect . . . " J. of Clin Investigation 106(10), pp. 1189-1195.
Nishiyama et al. (1999) "Identification of Thioredoxin-Binding Protein-2/Vitamin D3 Up-Regulated Protein 1 as a Negative . . . " J Biol. Chem. 274(31), pp. 21645-21650.
Pak, J.H. et al. (2002) "An antisense Oligonucleotides to 1-cys Peroxiredoxin Causes Lipid Peroxidation and Apoptosis in Lung . . . " J. Bio Chem, 277(51), pp. 49927-49934.
Park, S. et al. (2000) "Antisense of Human Peroxiredoxin II Enhances Radiation-Induced Cell Death" Clin Cancer Research 6, pp. 4915-4920.
Rinn et al. (2006) "Anatomic Demarcation by Positional Variation in Fibroblast Gene Expression Programs" PLOS Genetics 2(7), pp. 1084-1096.
Xiang et al. (2005) "Catalytic Degradation of Vitamin D Up-Regulated Protein 1 mRNA Enhances Cardiomyocytes Survival and Prevents . . . " J Biol Chem 280(47), pp. 39394-39402.
Berk, B. (2007) "Novel Approaches to Treat Oxidative Stress and Cardiovascular Disease" Tans. Am. Clin. Clim. Assoc. 118, pp. 209-214.
Prosperi et al. (1993), "A Human cDNA Corresponding to a Gene Overexpressed during Cell Proliferation Encodes a Product Sharing . . . " J. Biol. Chem., 268(15), pp. 11050-11056.
Smith, W. (1991) "Interleukin-8 induces Neutrophil Transendothelial Migration" Immunology 72, pp. 65-72.
Dec. 23, 2009 Final Office Action issued in connection with U.S. Appl. No. 11/894,581.
Takahashi et al. (1995) "Effects of Endothelial Interleukin-8 on Neutrophil Migration Across an Endothelial Monolayer," Cardiovasc. Res. 29:670-675.
Dec. 29, 2009 Final Office Action issued in connection with U.S. Appl. No. 11/648,769.
Kang et al. (1998) "Mammalian Peroxiredoxin Isoforms can Reduce Hydrogen Peroxide Generated in Response to Growth Factors and Tumor Necrosis Factor-Alpha," Journal of Bio.
Zhang et al. (1997) "Thioredoxin Peroxidase in a Novel Inhibitor of Apoptosis with a Mechanism Distinct from that of BCL-2," Journal of Biological 272(49):30615-8.
Berggren et al. (2001) "Thioredoxin Peroxidase-1 (Peroxiredoxin-1) is Increased in Thioredoxin-1 Transfected Cells . . . " Archives of Biochemistry and Biophysics 392(1):103-9.

\* cited by examiner

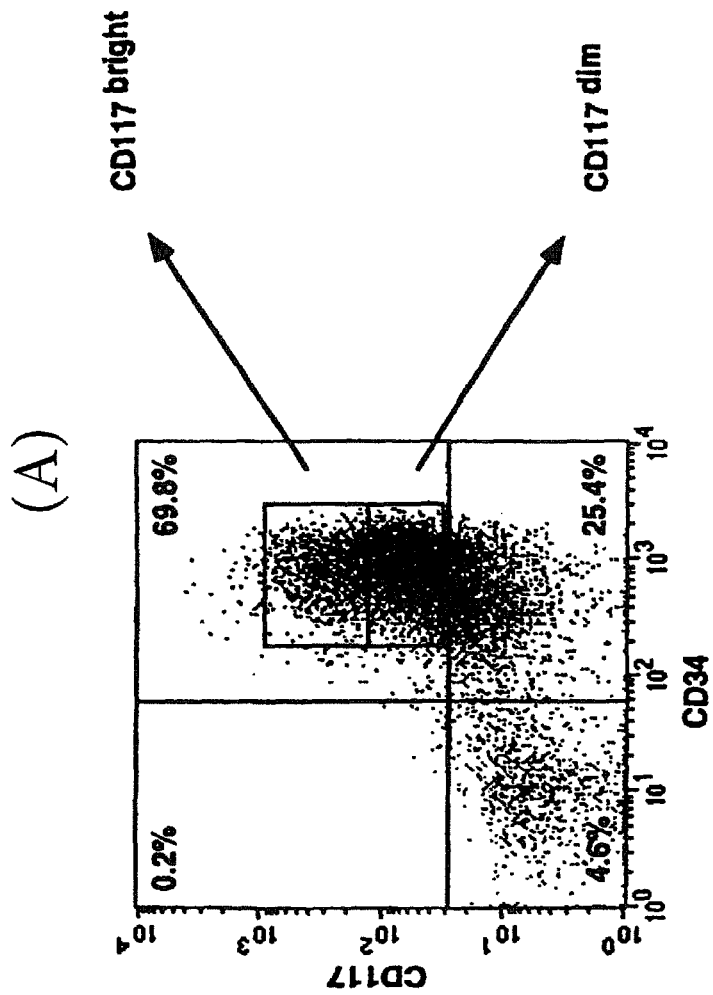

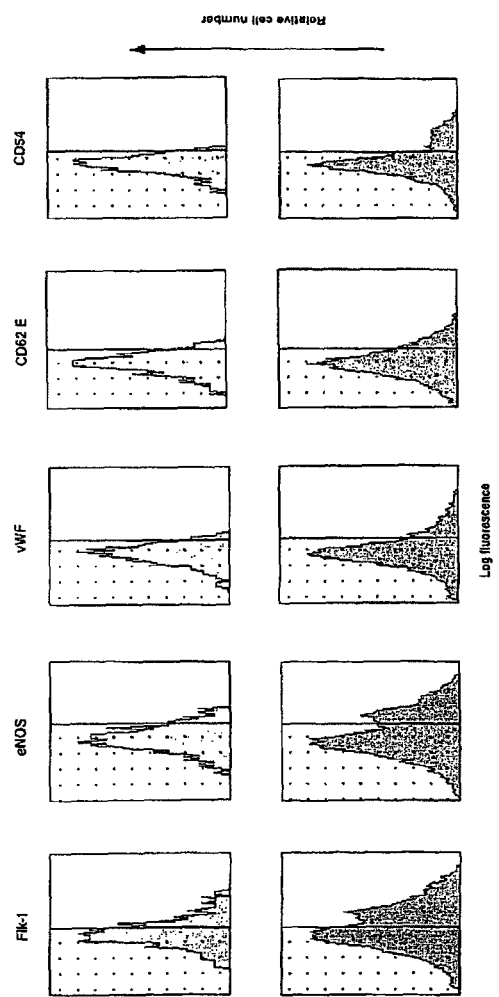
Fig. 1 (cont.) (B)

(D)

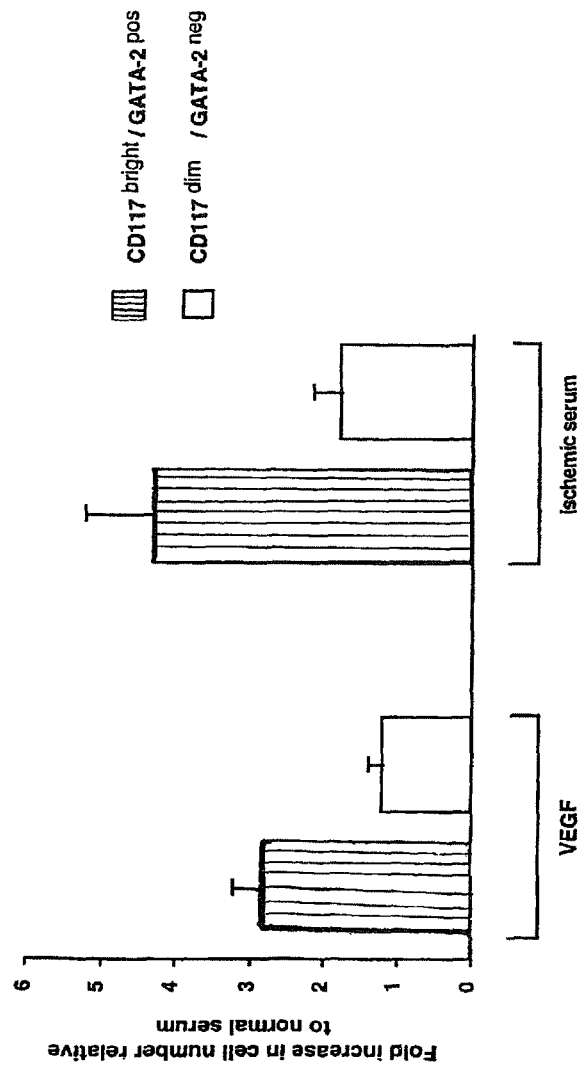

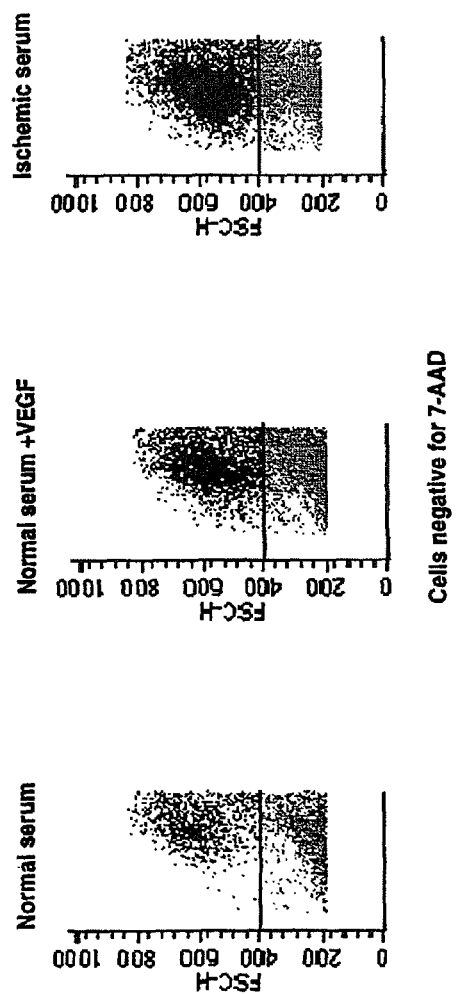
Fig. 2 (cont.) (B)

(A)

(B)

(C)

(D)

(E)

FIGURE 4E
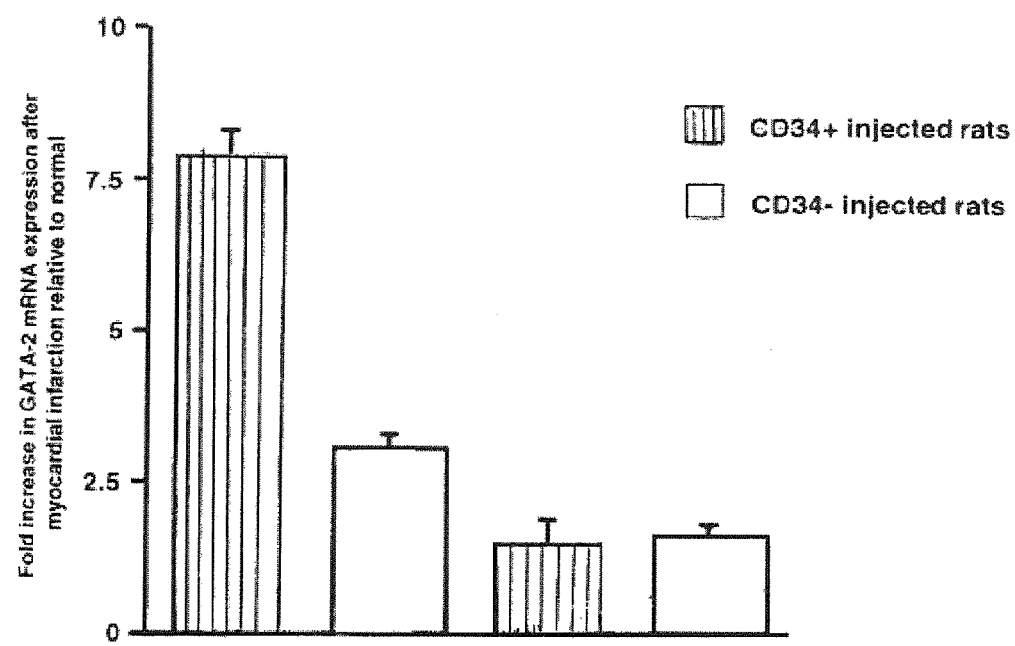
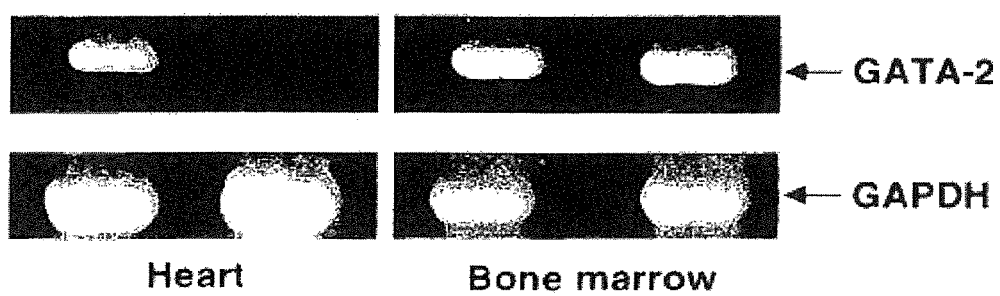

(B)

(C)

(D)

(A)

(B)

(C)

(D)

Fig. 6 (cont.)
(E)

Fig. 6 (cont.)
(F)

(G)

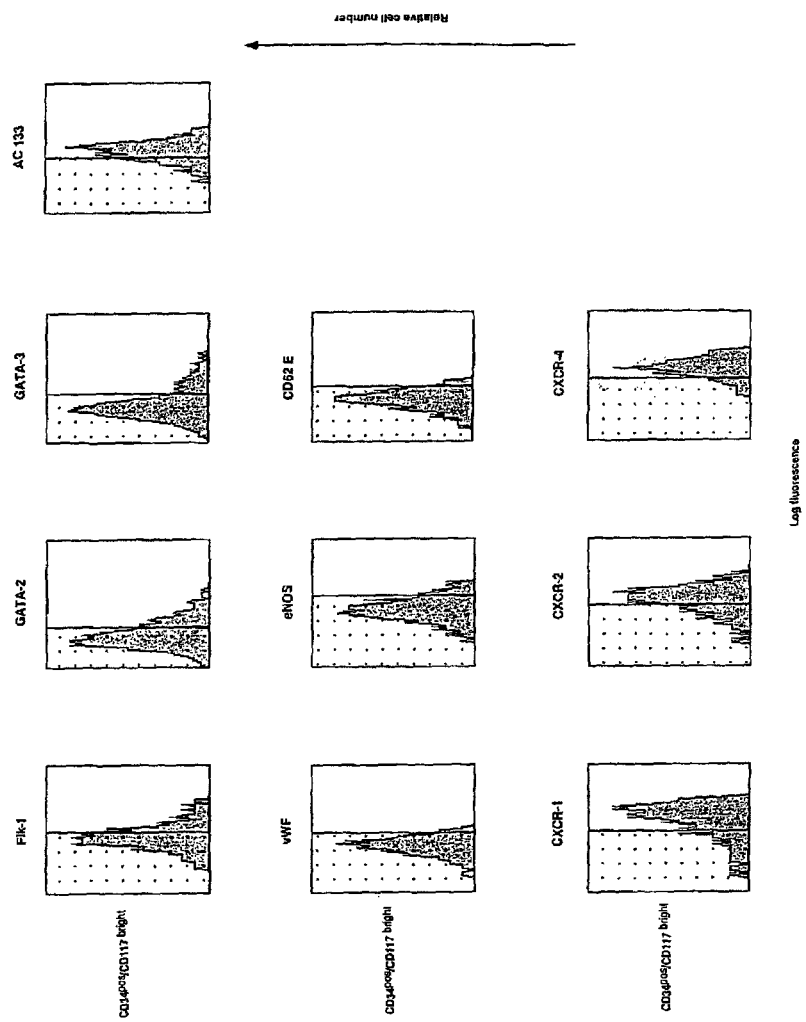

Fig. 7 (cont.)
(B)
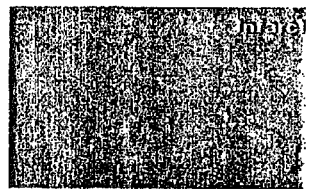 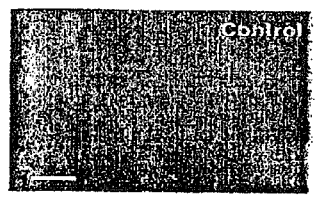

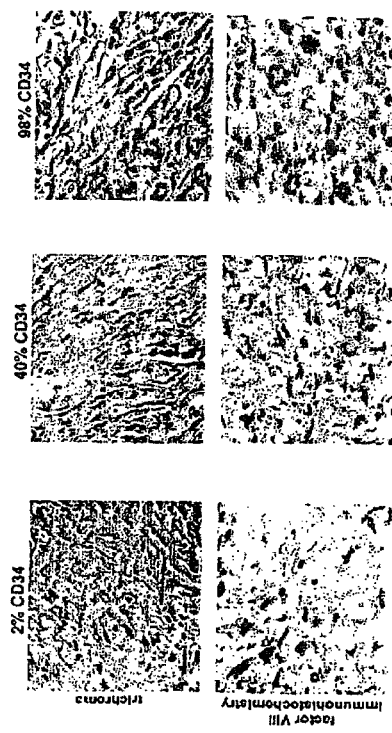
Fig. 7 (cont.) (C)

(A)

(B)

(C)

(D)

(E)

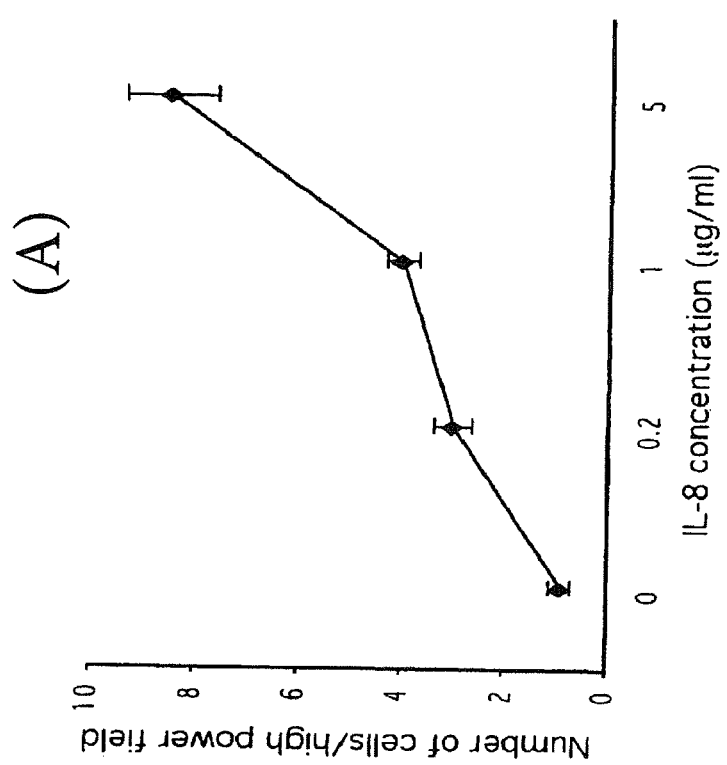

(B)

(C)

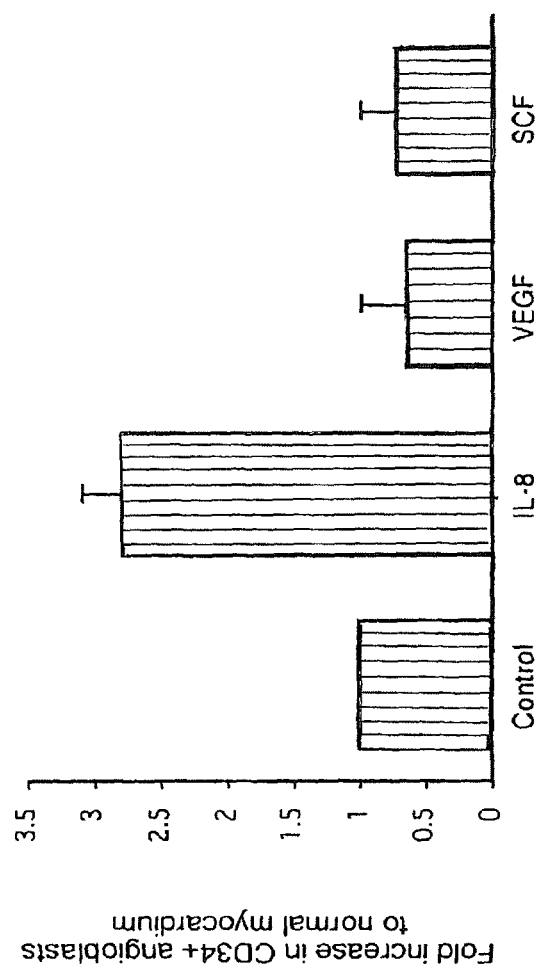

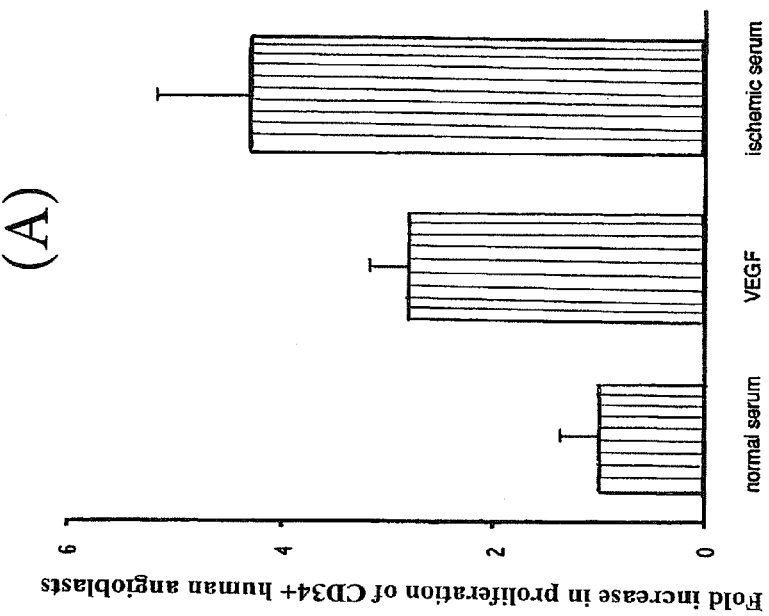

(B)

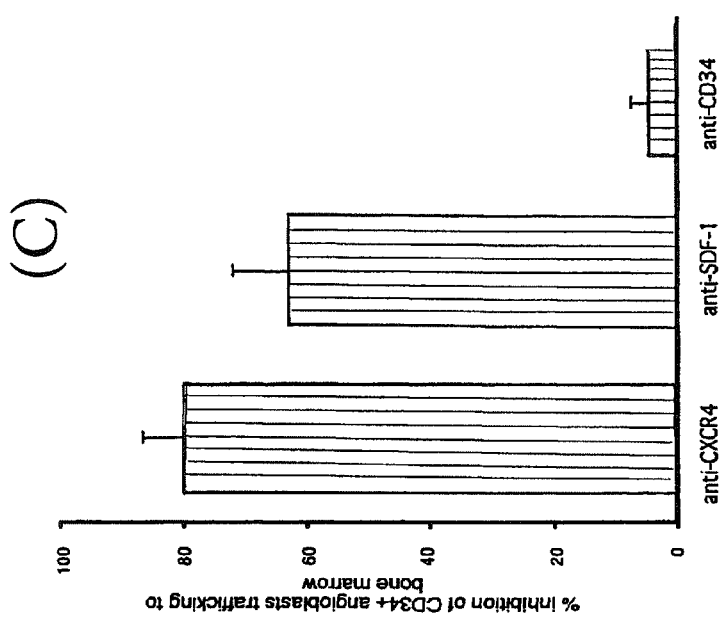

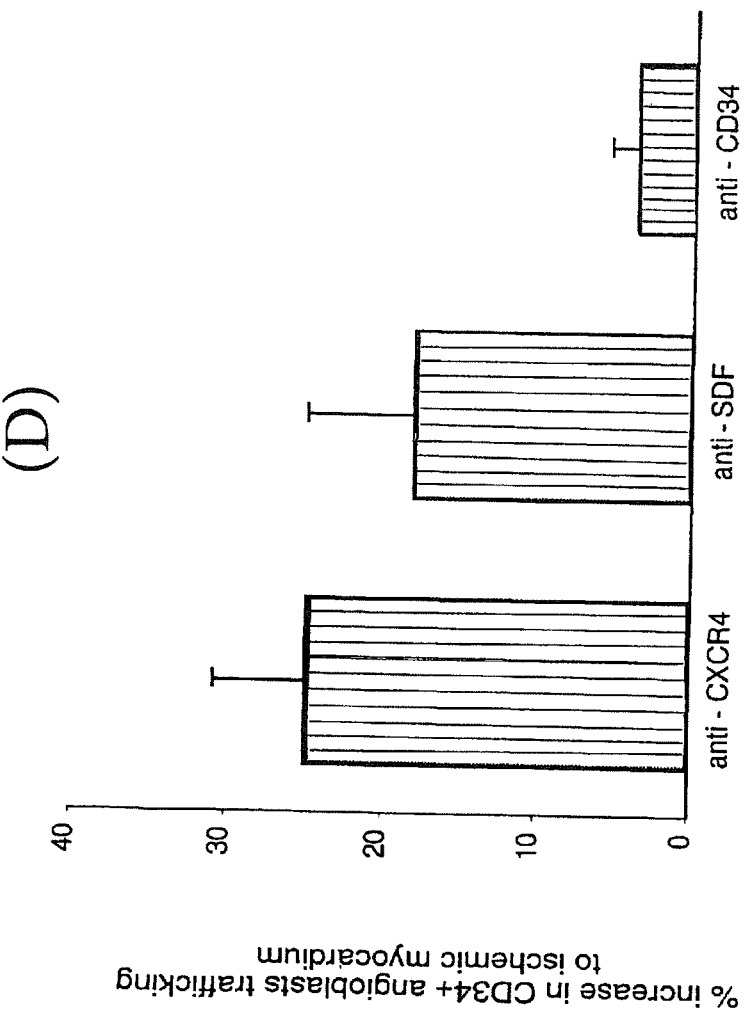
Fig. 10 (cont.) (D)

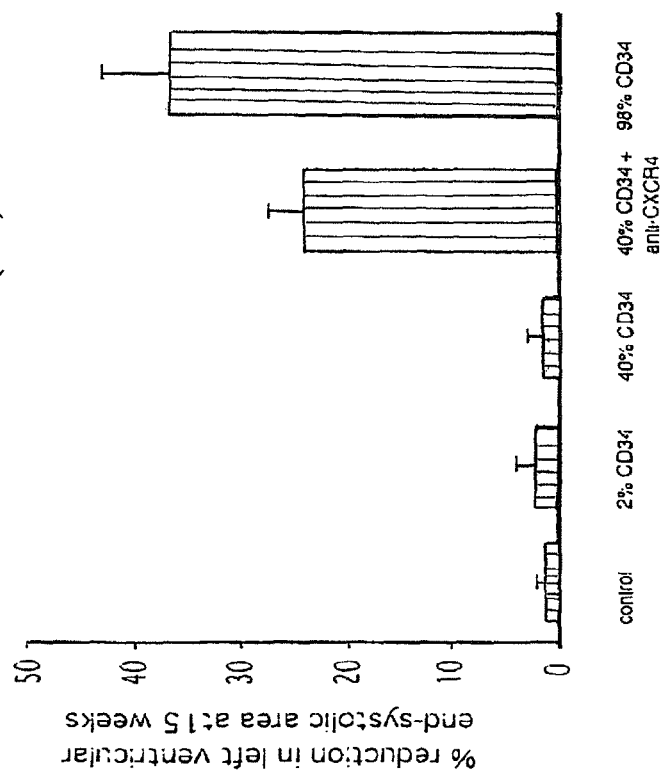

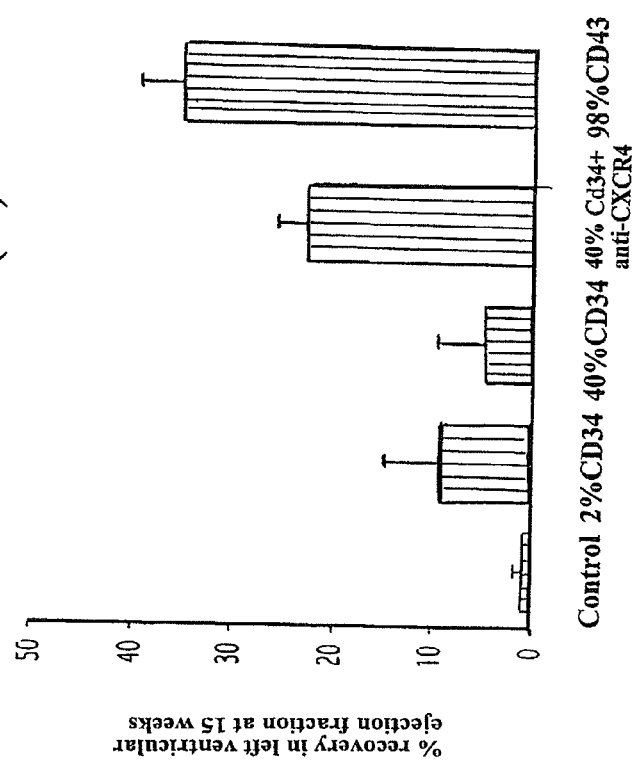

(C)

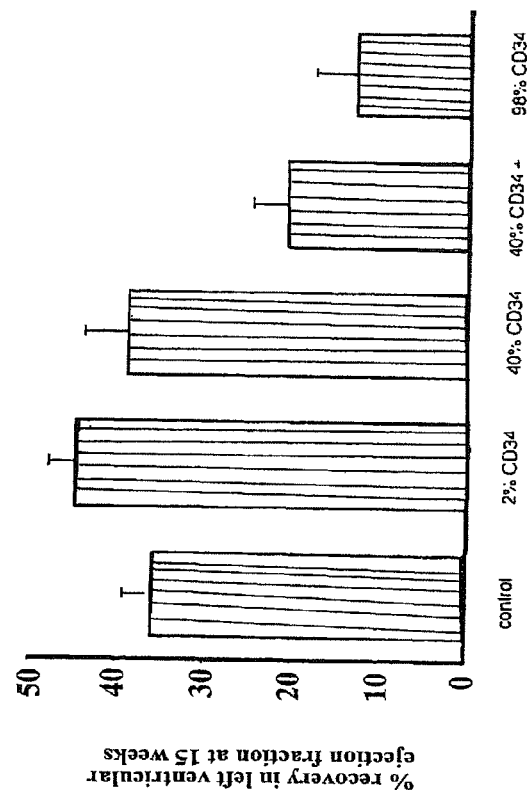

USE OF SDF-1 TO IMPROVE ISCHEMIC MYOCARDIAL FUNCTION

This application is a continuation of U.S. Ser. No. 12/657,264, filed Jan. 15, 2010, now U.S. Pat. No. 8,486,416, which is a continuation of U.S. Ser. No. 11/234,879, filed Sep. 22, 2005, now U.S. Pat. No. 7,662,392, issued Feb. 16, 2010, which is a continuation of U.S. Ser. No. 10/220,554, filed Mar. 4, 2003, now abandoned, which is a §371 national stage of PCT International Application No. PCT/US2001/018399, filed Jun. 5, 2001, which is a continuation-in-part and claims the benefit of U.S. Ser. No. 09/587,441, filed Jun. 5, 2000, now abandoned, the contents of which are hereby incorporated by reference.

Throughout this application, various references are referred to within parentheses. Disclosures of these publications in their entireties are hereby incorporated by reference into this application to more fully describe the state of the art to which this invention pertains. Full bibliographic citation for these references may be found at the end of this application, preceding the claims.

BACKGROUND OF THE INVENTION

Left ventricular remodeling after myocardial infarction is a major cause of subsequent heart failure and death. The capillary network cannot keep pace with the greater demands of the hypertrophied but viable myocardium, resulting in myocardial death and fibrous replacement. The first series of experiments of the present invention, described below, show that human adult bone marrow contains endothelial cell precursors with phenotypic and functional characteristics of embryonic hemangioblasts, and that these can be mobilized, expanded, and used to induce infarct bed vasculogenesis after experimental myocardial infarction. The neo-angiogenesis results in significant and sustained increase in viable myocardial tissue, reduction in collagen deposition, and improved myocardial function. The use of cytokine-mobilized autologous human bone marrow-derived angioblasts for revascularization of myocardial infarct tissue, alone or in conjunction with currently used therapies, offers the potential to significantly reduce morbidity and mortality associated with left ventricular remodeling post-myocardial infarction.

Although prompt reperfusion within a narrow time window has significantly reduced early mortality from acute myocardial infarction, post-infarction heart failure is increasing and reaching epidemic proportions (1). Left ventricular remodeling after myocardial infarction, characterized by expansion of the initial infarct area, progressive thinning of the wall surrounding the infarct, and dilation of the left ventricular lumen, has been identified as a major prognostic factor for subsequent heart failure (2,3). This process is accompanied by transcription of genes normally expressed only in the fetal state, rapid and progressive increase in collagen secretion by cardiac fibroblasts, deposition of fibrous tissue in the ventricular wall, increased wall stiffness, and both diastolic and systolic dysfunction (4,5). Hypoxia directly stimulates collagen secretion by cardiac fibroblasts, while inhibiting DNA synthesis and cellular proliferation (6). In animal models, late reperfusion following experimental myocardial infarction at a point beyond myocardial salvage significantly benefits remodeling (7). Moreover, the presence of a patent infarct related artery is consistently associated with survival benefits in the post-infarction period in humans (8). This appears to be due to adequate reperfusion of the infarct vascular bed which modifies the ventricular remodeling process and prevents abnormal changes in wall motion (9).

Successful reperfusion of non-cardiac tissues rendered ischemic in experimental animal models has recently been demonstrated by use of either circulating or bone marrow-derived cellular elements (10-13). Although the precise nature of these cells was not defined in these studies, the presence of precursor cells in both adult human circulation and bone marrow which have the capability to differentiate into functional endothelial cells, a process termed vasculogenesis (14-16), has been shown. In the pre-natal period, precursor cells derived from the ventral endothelium of the aorta in human and lower species have been shown to give rise to cellular elements involved in both the processes of vasculogenesis and hematopoiesis (17,18). These cells have been termed embryonic hemangioblasts, are characterized by expression of CD34, CD117 (stem cell factor receptor), Flk-1 (vascular endothelial cell growth factor receptor-2, VEGFR-2), and Tie-2 (angiopoietin receptor), and have been shown to have high proliferative potential with blast colony formation in response to VEGF (19-22). The subsequent proliferation and differentiation of embryonic hemangioblasts to adult-type pluripotent stem cells appears to be related to co-expression of the GATA-2 transcription factor, since GATA-2 knockout embryonic stem cells have a complete block in definitive hematopoiesis and seeding of the fetal liver and bone marrow (23). Moreover, the earliest precursor of both hematopoietic and endothelial cell lineage to have diverged from embryonic ventral endothelium has been shown to express VEGF receptors as well as GATA-2 and alpha4-integrins (24). The first series of experiments of the present invention shows that GATA-2 positive stem cell precursors are also present in adult human bone marrow, demonstrate properties of hemangioblasts, and can be used to induce vasculogenesis, thus preventing remodeling and heart failure in experimental myocardial infarction.

Growth of new vessels from pre-existing mature endothelium has been termed angiogenesis, and can be regulated by many factors including certain CXC chemokines (47-50). In contrast, vasculogenesis is mediated by bone marrow-derived endothelial precursors (51-53) with phenotypic characteristics of embryonic angioblasts and growth/differentiation properties regulated by receptor tyrosine kinases such as vascular endothelial growth factor (VEGF) (54-57). Therapeutic vasculogenesis (58-62) has the potential to improve perfusion of ischemic tissues, however the receptor/ligand interactions involved in selective trafficking of endothelial precursors to sites of tissue ischemia are not known. The second series of experiments of the present invention, described below, show that vasculogenesis can develop in infarcted myocardium as a result of interactions between CXC receptors on human bone marrow-derived angioblasts and ELR-positive CXC chemokines induced by ischemia, including IL-8 and Gro-alpha. Moreover, redirected trafficking of angioblasts from the bone marrow to ischemic myocardium can be achieved by blocking CXCR4/SDF-1 interactions, resulting in increased vasculogenesis, decreased myocardial death and fibrous replacement, and improved cardiac function. The results of the experiments indicate that CXC chemokines, including IL-8, Gro-alpha, and stromal-derived factor-1 (SDF-1), play a central role in regulating vasculogenesis in the adult human, and suggest that manipulating interactions between CXC chemokines and their receptors on bone marrow-derived angioblasts can lead to optimal therapeutic vasculogenesis and salvage of ischemic tissues. The third series of experiments, described below, show that CC chemokines also play a role in mediating angioblast chemotaxis to ischemic myocardium.

The angiogenic response during wound repair or inflammation is thought to result from changes in adhesive interactions between endothelial cells in pre-existing vasculature and extracellular matrix which are regulated by locally-produced factors and which lead to endothelial cell migration, proliferation, reorganization and microvessel formation (70). The human CXC chemokine family consists of small (<10 kD) heparin-binding polypeptides that bind to and have potent chemotactic activity for endothelial cells. Three amino acid residues at the N-terminus (Glu-Leu-Arg, the ELR motif) determine binding of CXC chemokines such as IL-8 and Gro-alpha to CXC receptors 1 and 2 on endothelial cells (49,71), thus promoting endothelial chemotaxis and angiogenesis (47-48). In contrast, CXC chemokines lacking the ELR motif bind to different CXC receptors and inhibit growth-factor mediated angiogenesis (49-72). Although SDF-1, an ELR-negative CXC chemokine, is a potent inducer of endothelial chemotaxis through interactions with CXCR4 (73), its angiogenic effects appear to be limited to the developing gastrointestinal tract vascular system (50).

Vasculogenesis first occurs during the pre-natal period, with haemangioblasts derived from the human ventral aorta giving rise to both endothelial and haematopoietic cellular elements (74,75). Similar endothelial progenitor cells have recently) been identified in adult human bone marrow (51-53), and shown to have the potential to induce vasculogenesis in ischemic tissues (59-61). However, the signals from ischemic sites required for chemoattraction of such bone marrow-derived precursors, and the receptors used by these cells for selective trafficking to these sites, are unknown. Following myocardial infarction a process of neoangiogenesis occurs (62,63); but is insufficient to sustain viable tissue undergoing compensatory hypertrophy, leading to further cell death, expansion of the initial infarct area, and collagen replacement (64-66). This process, termed remodeling, results in progressive heart failure (67-69). In the experiments described below, a nude rat model of myocardial infarction was used to investigate whether CXC chemokines containing the ELR motif regulate migration of human bone marrow-derived angioblasts to sites of tissue ischemia. Moreover, since selective bone marrow homing and engraftment of haematopoietic progenitors depends on CXCR4 binding to SDF-1 expressed constitutively in the bone marrow (76-78), whether interruption of CXCR4/SDF-1 interactions could redirect trafficking of human bone marrow-derived angioblasts to sites of tissue ischemia, thereby augmenting therapeutic vasculogenesis, was examined. The results of the experiments indicate that CXC chemokines, including IL-8, Gro-alpha, and SDF-1, play a central role in regulating human adult bone marrow-dependent vasculogenesis. Further, the fourth series of experiments described below show that stem cells can induce angiogenesis in peri-infarct tissue.

SUMMARY OF THE INVENTION

This invention provides a method of stimulating vasculogenesis in ischemia-damaged tissue of a subject comprising:
(a) removing stem cells from a location within the subject;
(b) recovering endothelial progenitor cells from the stem cells removed in step (a); and
(c) introducing the endothelial progenitor cells from step (b) into a different location within the subject such that the endothelial progenitor cells stimulate vasculogenesis in the subject's ischemia-damaged tissue.

This invention also provides the instant method, wherein subsequent to step (b), but before step (c), the endothelial progenitor cells are expanded by contacting them with a growth factor.

This invention also provides the instant method, wherein the growth factor is a cytokine.

This invention also provides the instant method, wherein the cytokine is VEGF, FGF, G-CSF, IGF, M-CSF, or GM-CSF.

This invention also provides the instant method, wherein the growth factor is a chemokine.

This invention also provides the instant method, wherein the chemokine is Interleukin-8.

This invention also provides the instant method, wherein the endothelial progenitor cells are separated from other stem cells before expansion.

This invention also provides the instant method, wherein the ischemia-damaged tissue is myocardium.

This invention also provides the instant method, wherein the ischemia-damaged tissue is nervous system tissue.

This invention also provides the instant method, wherein the stem cells are removed from the subject's bone marrow.

This invention also provides the instant method, wherein the removal of the stem cells from the bone marrow is effected by aspiration from the subject's bone marrow.

This invention also provides the instant method, wherein the removal of the stem cells from the subject is effected by a method comprising:
(a) introducing a growth factor into the subject to mobilize the stem cells into the subject's blood; and
(b) removing a sample of blood containing the stem cells from the subject.

This invention also provides the instant method, wherein the growth factor is introduced into the subject subcutaneously, orally, intravenously or intramuscularly.

This invention also provides the instant method, wherein the growth factor is a chemokine that induces mobilization.

This invention also provides the instant method, wherein the chemokine is Interleukin-8.

This invention also provides the instant method, wherein the growth factor is a cytokine.

This invention also provides the instant method, wherein the cytokine is G-CSF, M-CSF, or GM-CSF.

This invention also provides the instant method, wherein the endothelial progenitor cells are recovered based upon their expression of CD117.

This invention also provides the instant method, wherein the endothelial progenitor cells are recovered based upon their expression of a GATA-2 activated gene product.

This invention also provides the instant method, wherein the endothelial progenitor cells are recovered based upon their expression of one or more of CD34, VEGF-R, Tie-2, GATA-3 or AC133.

This invention also provides the instant method, wherein the subject has suffered or is suffering from one or more of the following: myocardial infarction, chronic heart failure, ischemic heart disease, coronary artery disease, diabetic heart disease, hemorrhagic stroke, thrombotic stroke, embolic stroke, limb ischemia, or another disease in which tissue is rendered ischemic.

This invention also provides the instant method, wherein step (a) occurs prior to the subject suffering ischemia-damaged tissue and wherein step (c) occurs after the subject has suffered ischemia-damaged tissue.

This invention also provides the instant method, wherein the endothelial progenitor cells are frozen for a period of time between steps (b) and (c).

This invention also provides the instant method, wherein the endothelial progenitor cells are frozen for a period of time after being expanded but before step (c) is performed.

This invention also provides the instant method, wherein the endothelial progenitor cells are introduced into the subject by injection directly into the peripheral circulation, heart muscle, left ventricle, right ventricle, coronary artery, cerebro-spinal fluid, neural tissue, ischemic tissue, or post-ischemic tissue.

This invention also provides the instant method, further comprising administering to the subject one or more of the following: an inhibitor of Plasminogen Activator Inhibitor, Angiotensin Converting Enzyme Inhibitor or a beta blocker, wherein such administration occurs prior to, concomitant with, or following step (c).

This invention also provides a method of stimulating angiogenesis in peri-infarct tissue in a subject comprising:
(a) removing stem cells from a location within a subject;
(b) recovering endothelial progenitor cells from the stem cells removed in step (a);
(c) expanding the endothelial progenitor cells recovered in step (b) by contacting the progenitor cells with a growth factor; and
(d) introducing the expanded endothelial progenitor cells from step (c) into a different location in the subject such that the endothelial progenitor cells stimulate angiogenesis in peri-infarct tissue in the subject.

This invention also provides a method of selectively increasing the trafficking of endothelial progenitor cells to ischemia-damaged tissue in a subject comprising:
(a) administering endothelial progenitor cells to a subject; and
(b) administering a chemokine to the subject so as to thereby attract the endothelial progenitor cells to the ischemia-damaged tissue.

This invention also provides the instant method, wherein the chemokine is administered to the subject prior to administering the endothelial progenitor cells.

This invention also provides the instant method, wherein the chemokine is administered to the subject concurrently with the endothelial progenitor cells.

This invention also provides the instant method, wherein the chemokine is administered to the subject after administering the endothelial progenitor cells.

This invention also provides the instant method, wherein the chemokine is a CXC chemokine.

This invention also provides the instant method, wherein the CXC chemokine is selected from the group consisting of Interleukin-8, Gro-Alpha, or Stromal-Derived Factor-1.

This invention also provides the instant method, wherein the chemokine is a CC chemokine.

This invention also provides the instant method, wherein the CC chemokine is selected from the group consisting of RANTES, EOTAXIN, MCP-1, MCP-2, MCP-3, or MCP-4.

This invention also provides the instant method, wherein the chemokine is administered to the subject by injection into the subject's peripheral circulation, heart muscle, left ventricle, right ventricle, coronary arteries, cerebro-spinal fluid, neural tissue, ischemic tissue, or post-ischemic tissue.

This invention also provides a method of increasing trafficking of endothelial progenitor cells to ischemia-damaged tissue in a subject comprising inhibiting any interaction between Stromal-Derived Factor-1 and CXCR4.

This invention also provides the instant method, wherein interaction between Stromal-Derived Factor-1 (SDF-1) and CXCR4 is inhibited by administration of an anti-SDF-1 or an anti-CXCR4 monoclonal antibody to the subject.

This invention also provides the instant method, further comprising administering to the subject an angiotensin converting enzyme inhibitor, an $AT_1$-receptor blocker, or a beta blocker.

This invention also provides a method of reducing trafficking of endothelial progenitor cells to bone marrow in a subject comprising inhibiting production of Stromal-Derived Factor-1 in the subject's bone marrow.

This invention also provides the instant method, wherein SDF-1 production is inhibited by administration of an anti-SDF-1 or anti-CXCR4 monoclonal antibody to the subject.

This invention also provides a method for treating a cancer in a subject comprising administering to the subject a monoclonal antibody directed against an epitope of a specific chemokine produced by proliferating cells associated with the cancer so as to reduce trafficking of endothelial progenitor cells to such proliferating cells and thereby treat the cancer in the subject.

This invention also provides a method for treating a cancer in a subject comprising administering to the subject a monoclonal antibody directed against an epitope of a specific receptor located on an endothelial progenitor cell, for a chemokine produced by proliferating cells associated with the cancer, so as to reduce trafficking of the endothelial progenitor cell to such proliferating cells and thereby treat the cancer in the subject.

This invention also provides a method for treating a tumor in a subject comprising administering to the subject an antagonist to a specific receptor on an endothelial progenitor cell so as to reduce the progenitor cell's ability to induce vasculogenesis in the subject's tumor and thereby treat the tumor.

This invention also provides a method for treating a tumor in a subject comprising administering to the subject an antagonist to a specific receptor on an endothelial progenitor cell so as to reduce the progenitor cell's ability to induce angiogenesis in the subject's tumor and thereby treat the tumor.

This invention also provides the instant method, wherein the receptor is a CD117 receptor.

This invention also provides a method for expressing a gene of interest in an endothelial progenitor cell or a mast progenitor cell which comprises inserting into the cell a vector comprising a promoter containing a GATA-2 motif and the gene of interest.

This invention also provides the instant method, wherein the vector is inserted into the cell by transfection.

This invention also provides the instant method, wherein the promoter is a preproendothelin-1 promoter.

This invention also provides the instant method, wherein the promoter is of mammalian origin.

This invention also provides the instant method, wherein the promoter is of human origin.

This invention provides a composition comprising an amount of a monoclonal antibody directed against an epitope of a specific chemokine produced by a cancer effective to reduce trafficking of endothelial progenitor cells to the cancer, and a pharmaceutically acceptable carrier.

This invention provides a method of treating an abnormality in a subject wherein the abnormality is treated by the expression of a GATA-2 activated gene product in the subject comprising:
(a) removing stem cells from a location within the subject;
(b) recovering endothelial progenitor cells from the stem cells removed in step (a);
(c) recovering those endothelial progenitor cells recovered in step (b) that express GATA-2;

(d) inducing the cells recovered in step (c) as expressing GATA-2 to express a GATA-2 activated gene product; and
(e) introducing the cells expressing a GATA-2 activated gene product from step (d) into a different location in the subject such as to treat the abnormality.

This invention provides a method of treating an abnormality in a subject wherein the abnormality is treated by the expression of a GATA-2 activated gene product in the subject comprising:
(a) removing stem cells from a location within the subject;
(b) recovering mast progenitor cells from the stem cells removed in step (a);
(c) recovering those mast progenitor cells recovered in step (b) that express GATA-2;
(d) inducing the cells recovered in step (c) as expressing GATA-2 to express a GATA-2 activated gene product; and
(e) introducing the cells expressing a GATA-2 activated gene product from step (d) into a different location in the subject such as to treat the abnormality This invention provides the instant method, wherein the abnormality is ischemia-damaged tissue.

This invention provides the instant method, wherein the gene product is proendothelin.

This invention provides the instant method, wherein the gene product is endothelin.

This invention provides the a method of improving myocardial function in a subject that has suffered a myocardial infarct comprising:
(a) removing stem cells from a location in the subject;
(b) recovering cells that express CD117 from the stem cells; and
(c) introducing the recovered cells into a different location in the subject such that the cells improve myocardial function in the subject.

This invention provides the instant methods, wherein the subject is of mammalian origin.

This invention provides the instant method, wherein the mammal is of human origin.

This invention also provides a method of stimulating vasculogenesis in ischemia-damaged tissue in a subject comprising:
(a) obtaining allogeneic stem cells;
(b) recovering endothelial progenitor cells from the stem cells removed in step (a); and
(c) introducing the endothelial progenitor cells recovered in step (b) into the subject such that the endothelial progenitor cells stimulate vasculogenesis in the subject's ischemia-damaged tissue.

This invention provides the instant method, wherein the allogeneic stem cells are obtained from embryonic, fetal or cord blood sources.

This invention provides a method of stimulating angiogenesis in ischemia-damaged tissue in a subject comprising:
(a) obtaining allogeneic stem cells;
(b) recovering endothelial progenitor cells in the stem cells removed in step (a); and
(c) introducing the endothelial progenitor cells recovered in step (b) into the subject such that the endothelial progenitor cells stimulate angiogenesis in the subject's ischemia-damaged tissue.

This invention provides the instant method, wherein the allogeneic stem cells are obtained from embryonic, fetal or cord blood sources.

This invention also provides a method of improving myocardial function in a subject that has suffered a myocardial infarct comprising injecting G-CSF into the subject in order to mobilize endothelial progenitor cells.

This invention also provides a method of improving myocardial function in a subject that has suffered a myocardial infarct comprising injecting anti-CXCR4 antibody into the subject.

This invention also provides the instant method further comprising introducing endothelial progenitor cells into the subject.

This invention also provides the instant method further comprising introducing G-CSF into the subject in order to mobilize endothelial progenitor cells.

A-D depicts four-parameter flow cytometric phenotype characterization of G-CSF mobilized bone marrow-derived cells removed by leukopharesis from a representative human donor adult (25). Only live cells were analyzed, as defined by 7-AAD staining. For each marker used, shaded areas represent background log fluorescence relative to isoytype control antibody.
A. Following immunoselection of mononuclear cells (25), >95% of live cells express CD34.
B. The CD34+CD117$^{dim}$ subset contains a population with phenotypic characteristics of mature, vascular endothelium.
C. The CD34+CD117$^{bright}$ subset contains a population expressing markers characteristic of primitive hemangioblasts arising during waves of murine and human embryogenesis.
D. CD34+CD117$^{bright}$ cells co-expressing GATA-2 and GATA-3 also express AC133, another marker which defines hematopoietic cells with angioblast potential.

FIG. 2. Bone Marrow-Derived Angioblasts (BA) Have Greater Proliferative Activity In Response To Both VEGF And Ischemic Serum Than Bone Marrow-Derived Endothelial Cells (BMEC).

Depicted is the response of single-donor CD34-positive human cells sorted by a fluorescent GATA-2 mAb and cultured for 96 hours in RPMI with 20% normal rat serum, ischemic rat serum or 20 ng/ml VEGF. The numbers of CD117$^{bright}$GATA-2$^{pos}$ and CD117$^{dim}$ GATA-2$^{neg}$ cells were quantitated by both [$^3$H] thymidine uptake and by flow cytometry.
A. In comparison to culture in normal serum, the proliferative responses to either VEGF or ischemic serum were significantly higher for CD117$^{bright}$GATA-2$^{pos}$ BA relative to CD117$^{dim}$GATA-2$^{neg}$ BMEC from the same donor (both p<0.01)
B. The population expanded by culture with either VEGF or ischemic serum and characterized by multiparameter flow cytometric analysis as CD117$^{bright}$GATA-2$^{pos}$ consisted of large blast cells, as demonstrated by high forward scatter (fsc).
C. The expanded population of CD117$^{bright}$GATA-2$^{pos}$ cells did not demonstrate increased surface expression of mature endothelial cell markers after culture with VEGF in comparison to culture with normal medium, indicating blast proliferation without differentiation.

Figure 3:
Figure 3:
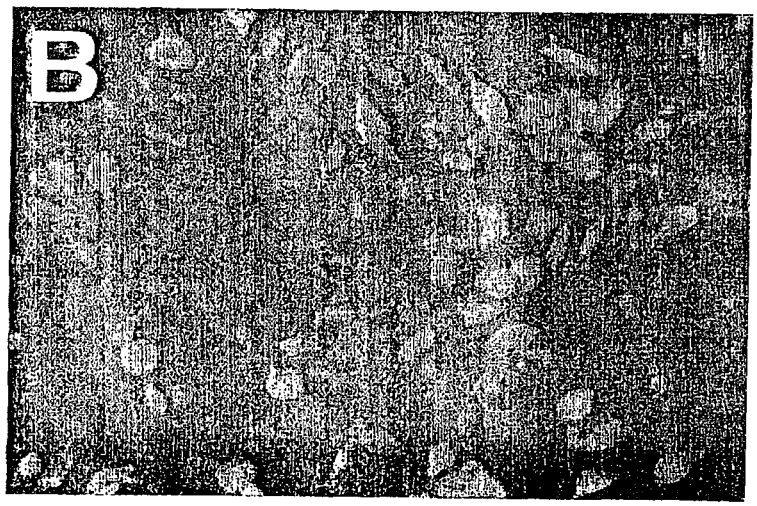
Figure 3:
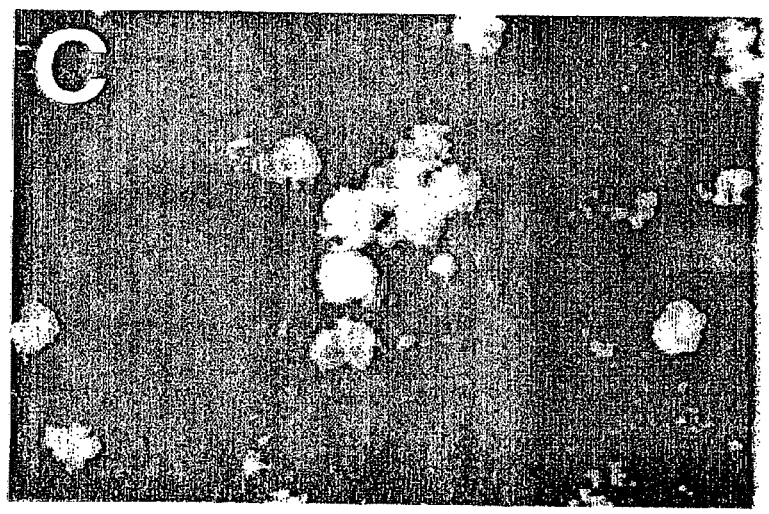
Figure 3:
Figure 3:

FIG. 3. Highly Purified Human Bone Marrow-Derived CD34 Cells Differentiate Into Endothelial Cells After in Vitro Culture.

Culture of highly-purified CD34+ human cells for 7 days in endothelial growth medium results in outgrowth of cells with morphologic and characteristic features of mature endothelial cell monolayers. The majority of the monolayers (>90%) demonstrate:

A. Exuberant cobblestone pattern of cellular proliferation and growth;
B. Uniform uptake of DiI-labeled acetylated LDL;
C. CD34 expression, as measured by immunofluorescence using a fluorescein-conjugated mAb;
D. Factor VIII expression, as measured by immunoperoxidase using a biotin-conjugated mAb; and
E. Expression of eNOS, determined by in situ hybridization using a specific probe.

FIG. 4. In vivo migratory and proliferative characteristics of bone marrow- and peripheral vasculature-derived human cells, after induction of myocardial ischemia.

A-C. Intravenous injection of $2 \times 10^6$ DiI-labeled human CD34-enriched cells (>95% CD34 purity), CD34-negative cells (<5% CD34 purity), or saphenous vein endothelial cells (SVEC), into nude rats after coronary artery ligation and infarction. Each human cellular population caused a similar degree of infiltration in infarcted rat myocardium at 48 hours.
D. A sham procedure, with no human cells found in the non-infarcted rat heart.
E. Measurement of human GATA-2 mRNA expression in the bone marrow and heart of infarcted rats receiving either CD34-positive cells (>95% CD34 purity), CD34-negative cells (<5% CD34 purity), normalized for total human RNA measured by GAPDH expression. GATA-2 mRNA in ischemic tissue is expressed as the fold increase above that present under the same experimental condition in the absence of ischemia. Bone marrow from ischemic rats receiving either CD34+ or CD34− cells contained similar levels of human GATA-2 mRNA, and showed a similar fold induction in GATA-2 mRNA expression after ischemia. In contrast, ischemic hearts of rats receiving CD34+ cells contained much higher levels of human GATA-2 mRNA than those receiving CD34− cells. Moreover, the degree of increase in GATA-2 mRNA expression after infarction was 2.6-fold higher for hearts infiltrated by CD34+ cells compared with CD34− cells, indicating that GATA-2+ cells within the CD34+ fraction selectively traffic to ischemic myocardium.
F. Consecutive sections of a blood vessel within the infarct bed of a nude rat two weeks after injection of human CD34+ cells. The vessel incorporates human endothelial cells, as defined by co-expression of DiI, HLA class I as measured by immunofluorescence using a fluorescein-conjugated mAb, and factor VIII, as measured by immunoperoxidase using a biotin-conjugated mAb.

Figure 5:
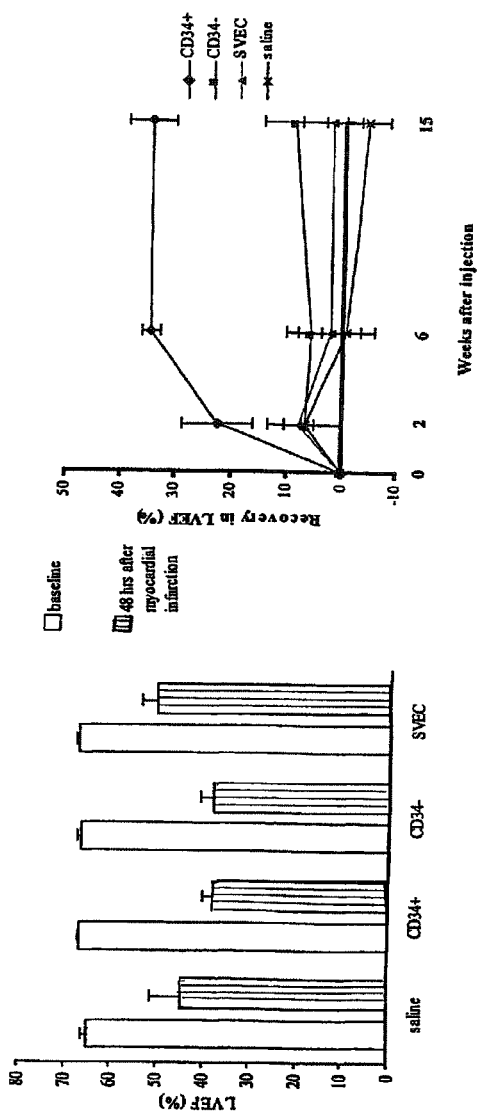
Figure 5:
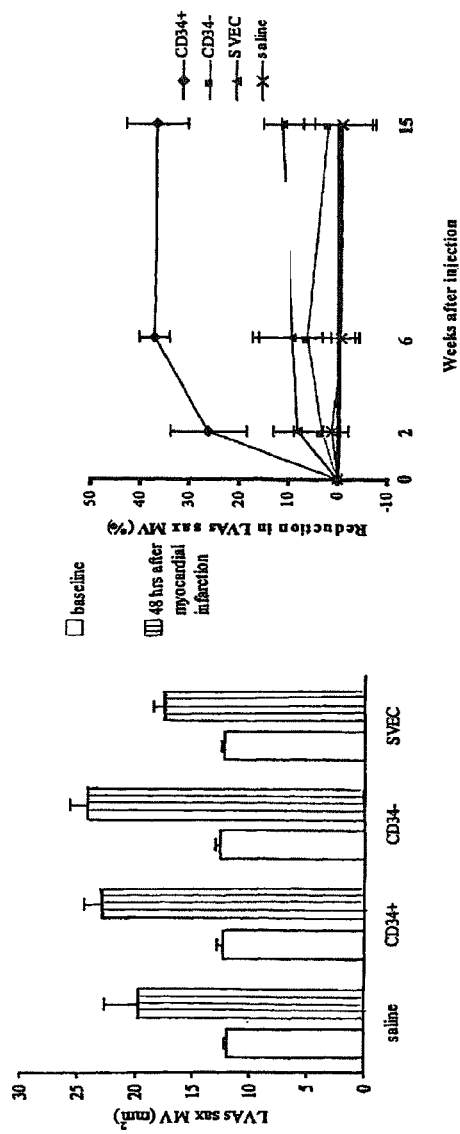
Figure 5:
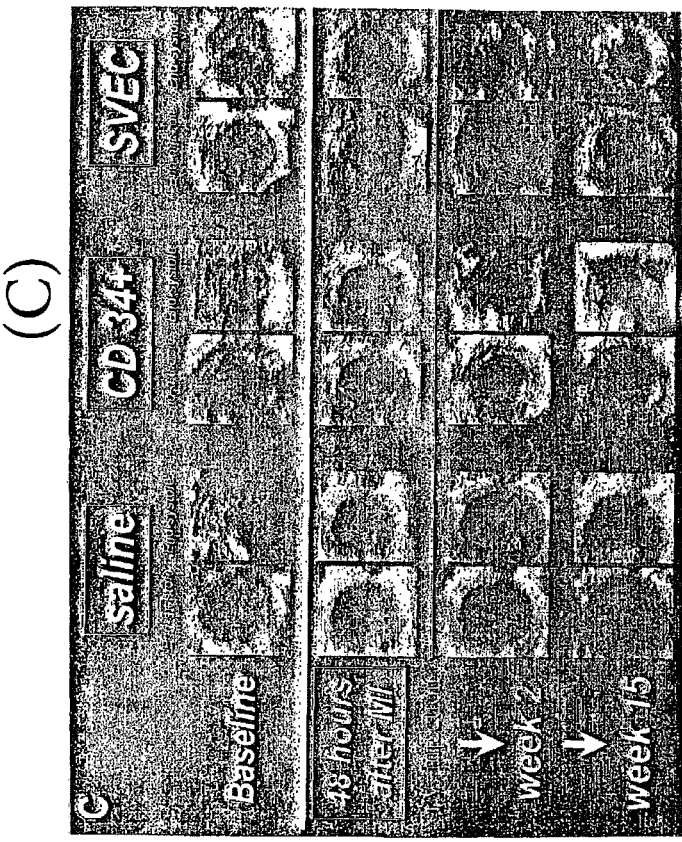
Figure 5:
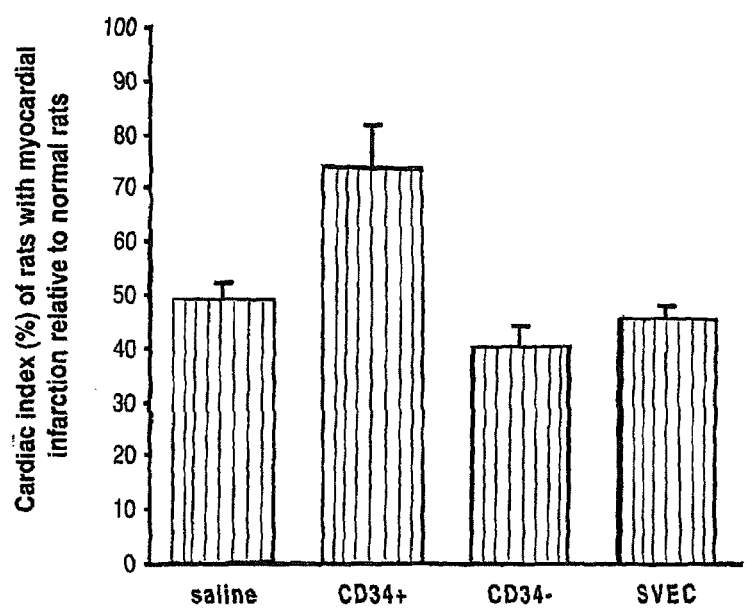

FIG. 5. Injection of G-CSF Mobilized Human CD34+ Cells Into Rata With Acute Infarction Improves Myocardial Function.

A-D compares the functional effects of injecting $2 \times 10^6$ G-CSF mobilized human CD34+ (>95% purity) cells, CD34− (<5% purity) cells, peripheral saphenous vein cells, or saline, into infarcted rat myocardium.
A. Although left ventricular ejection fraction (LVEF) was severely depressed in each group of recipients after LAD ligation, only injection of G-CSF mobilized adult human CD34+ cells was accompanied by significant, and sustained, LVEF recovery ($p<0.001$). LVEF recovery was calculated as the mean % improvement between LVEF after LAD ligation and pre-infarct LVEF.
B. Similarly, although left ventricular end-systolic area (LVAs) was markedly increased in each group of recipients after LAD ligation, only injection of G-CSF mobilized adult human CD34+ cells was accompanied by significant, and sustained, reduction in LVAs ($p<0.001$). Reduction in LVAs was calculated as the mean % improvement between LVAs after LAD ligation and pre-infarct LVAs.
C. Representative echocardiographic examples from each group are shown. At 48 hours after LAD ligation, diastolic function is severely compromised in each rat. At two weeks after injection, diastolic function is improved only in the rat receiving CD34+ cells. This effect persists at 15 weeks.
D. At 15 weeks post-infarction, rats injected with CD34+ cells demonstrated significantly less reduction in mean cardiac index relative to normal rats than each of the other groups ($p<0.001$).

Figure 6:
Figure 6:
Figure 6:
Figure 6:
Figure 6:
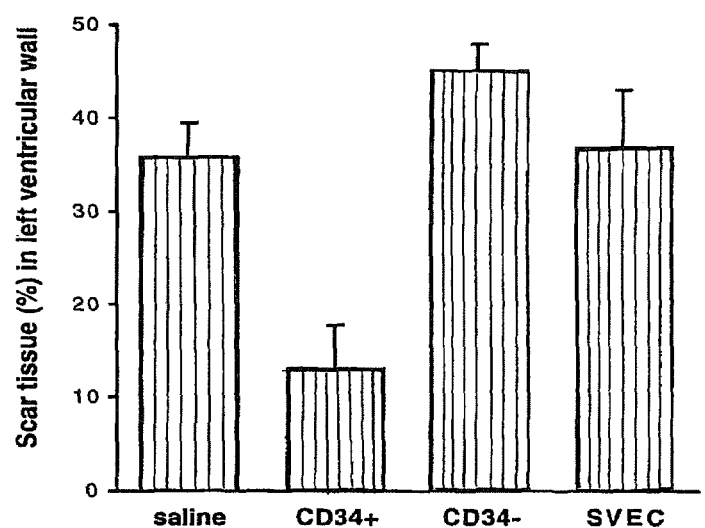

FIG. 6. Injection Of G-CSF Mobilized Human CD34+ Cells Into Rats With Acute Infarction Induces Neo-Angiogenesis And Modifies The Process Of Myocardian Remodeling.

A-D depicts infarcted rat myocardium at two weeks post-LAD ligation from representative experimental and control animals stained with either hematoxylin and eosin (A,B) or immunoperoxidase following binding of anti-factor VIII mAb (C,D). E,F depicts Mason trichrome stain of infarcted rat myocardium from representative control and experimental animals at 15 weeks post-LAD ligation. G depicts between-group differences in % scar/normal left ventricular tissue at 15 weeks.

A. Infarct zone of rat injected with human CD34+ cells demonstrates significant increase in microvascularity and cellularity of granulation tissue, numerous capillaries (arrowheads), feeding vessels (arrow), and decrease in matrix deposition and fibrosis (×200).
B. In contrast, infarct zone of control rat injected with saline shows a myocardial scar composed of paucicellular, dense fibrous tissue (arrows) (×200).
C. Ischemic myocardium of rat injected with human CD34+ cells demonstrates numerous factor VIII-positive interstitial angioblasts (arrows), and diffuse increase in factor VIII-positive capillaries (arrowheads) (×400).
D. Ischemic myocardium of rat injected with saline does not contain factor VIII-positive angioblasts (arrows), and demonstrates only focal areas of granulation tissue with factor VIII positive vascularity (arrowheads) (×400).
E. Trichrome stain of rat myocardium at 15 weeks post-infarction in rat injected with saline (×25). The collagen rich myocardial scar in the anterior wall of the left ventricle (ant.) stains blue and viable myocardium stains red. Focal islands of collagen deposition (blue) are also present in the posterior wall of the left ventricle (post). There is extensive loss of anterior wall myocardial mass, with collagen deposition and scar formation extending almost through the entire left ventricular wall thickness, causing aneurysmal dilatation and typical EKG abnormalities (persistent ST segment elevation).
F. In contrast, trichrome stain of rat myocardium at 15 weeks post-infarction in rat receiving highly purified CD34+ cells (×25) demonstrates significantly reduced infarct zone size together with increased mass of viable myocardium within the anterior wall (ant.) and normal EKG. Numerous vessels are evident at the junction of the infarct zone and viable myocardium. There is no focal collagen deposition in the left ventricular posterior wall (post).
G. Rats receiving CD34+ cells had a significant reduction in mean size of scar tissue relative to normal left ventricular myocardium compared with each of the other groups (p<0.01). Infarct size, involving both epicardial and endocardial regions, was measured with a planimeter digital image analyzer and expressed as a percentage of the total ventricular circumference at a given slice. For each animal, final infarct size was calculated as the average of 10-15 slices.

FIG. 7. Human Adult Bone Marrow-Derived Endothelial Precursor Cells Infiltrate Ischemic Myocardium, Inducing Infarct Bed Neoangiogenesis And Preventing Collagen Deposition.
- A. Four-parameter flow cytometric phenotypic characterization of G-CSF mobilized bone marrow-derived cells removed by leukopheresis from a representative human donor adult. Only live cells were analyzed, as defined by 7-AAD staining. For each marker used, shaded areas represent background log fluorescence relative to isotype control antibody. The CD34+CD117$^{bright}$ subset contains a population expressing markers characteristic of primitive haemangioblasts arising during waves of murine and human embryogenesis, but not markers of mature endothelium. These cells also express CXC chemokine receptors.
- B. DiI-labeled human CD34-enriched cells (>98% CD34 purity) injected intravenously into nude rats infiltrate rat myocardium after coronary artery ligation and infarction but not after sham operation at 48 hours.
- C. The myocardial infarct bed at two weeks post-LAD ligation from representative rats receiving 2.0×10$^6$ G-CSF mobilized human bone marrow-derived cells at 2%, 40%, or 98% CD34+ purity, and stained with either Masson's trichrome or immunoperoxidase. The infarct zones of rats receiving either 2% or 40% pure CD34+ cells show myocardial scars composed of paucicellular, dense fibrous tissue stained blue (×400). In contrast, the infarct zone of the rat injected with 98% pure human CD34+ cells demonstrates significant increase in microvascularity and cellularity of granulation tissue, numerous capillaries, and minimal matrix deposition and fibrosis (×400). Moreover, immunoperoxidase staining following binding of anti-factor VIII mAb shows that the infarct bed of the rat injected with 98% pure CD34+ cells demonstrates markedly increased numbers of factor VIII-positive capillaries, which are not seen in either of the other animals (×400).

Figure 8:
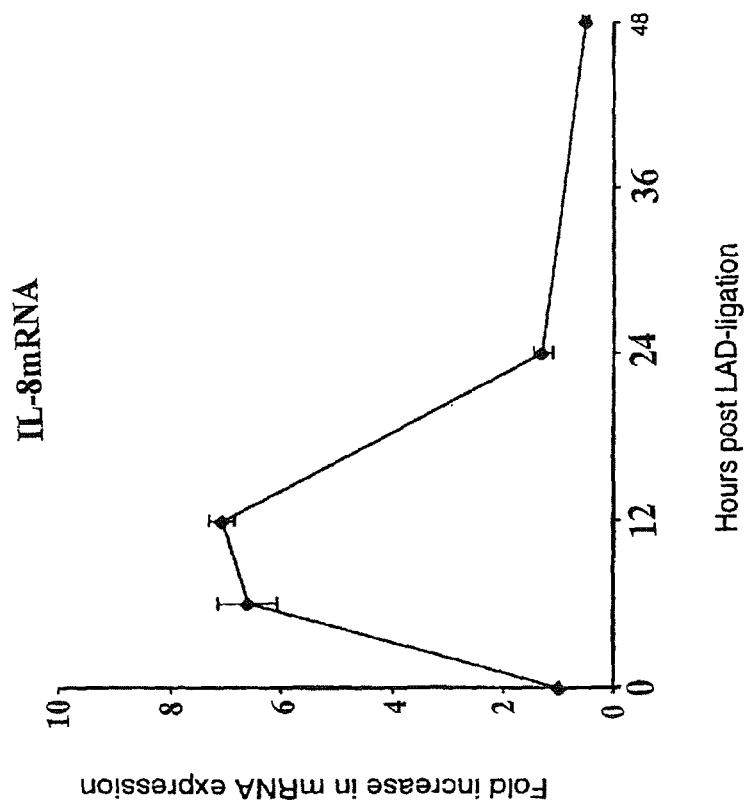
Figure 8:
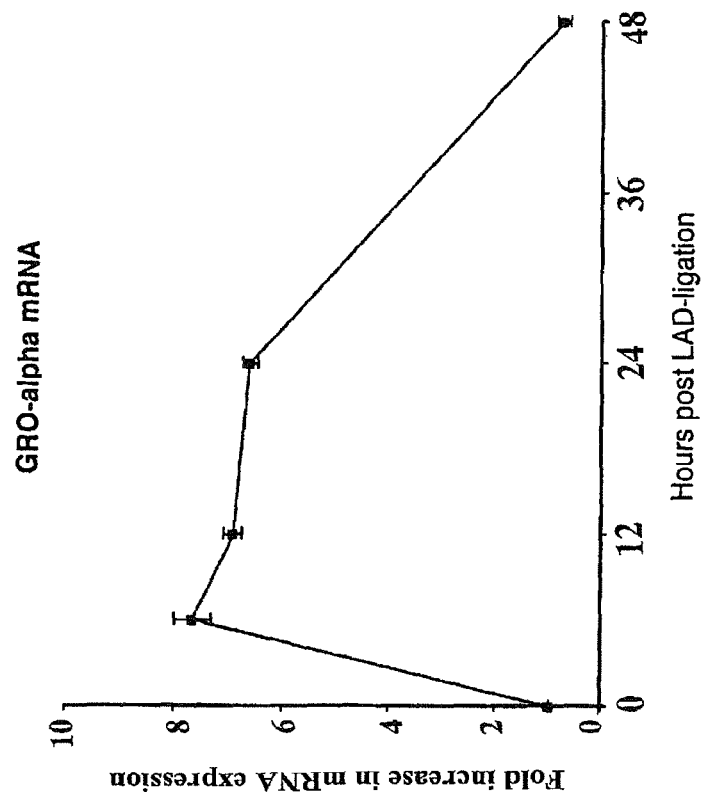
Figure 8:
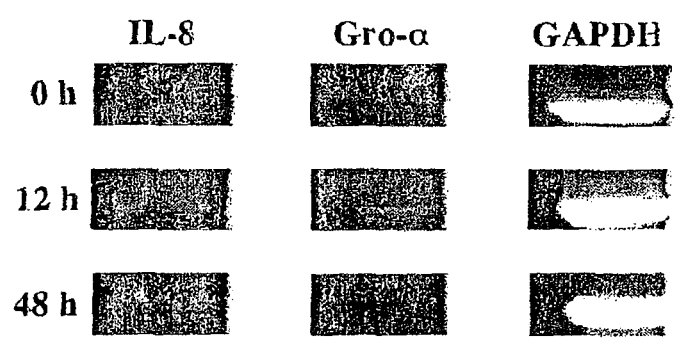
Figure 8:
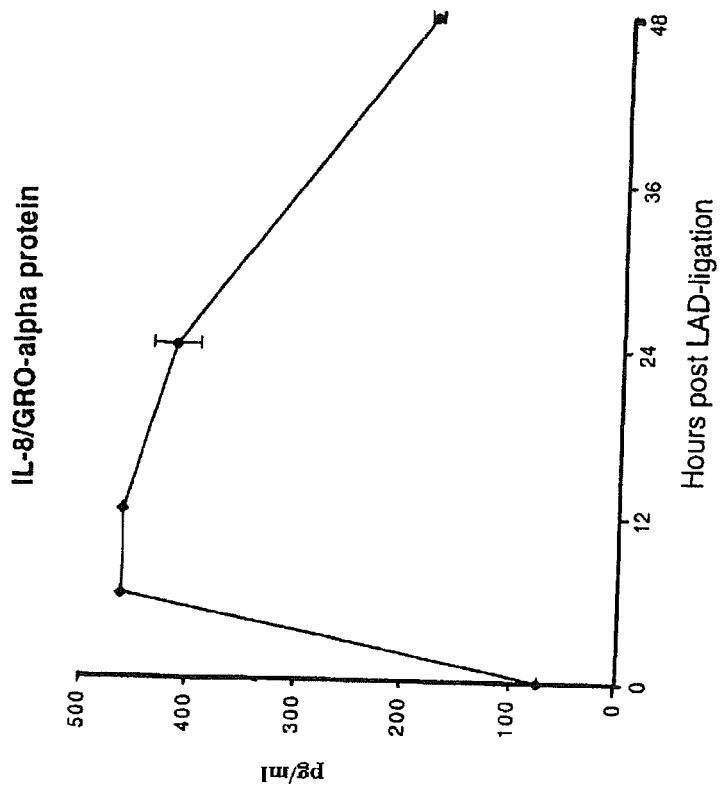
Figure 8:
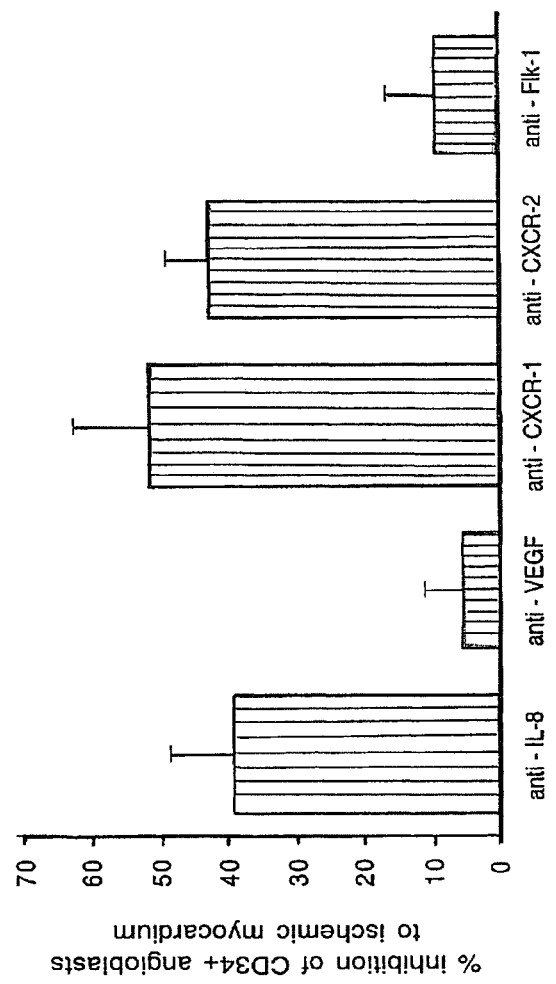

FIG. 8. Migration Of Human Bone Marrow-Derived Endothelial Precursor Cells To The Site Of Infarction Is Dependent On Interactions Between CXCR1/2 And IL-8/Gro-Alpha Induced By Myocardial Ischemia.
- A,B. Time-dependent increase in rat myocardial IL-8 and Gro-alpha mRNA expression relative to GAPDH from rats undergoing LAD ligation.
- C. IL-8, Gro-alpha, and GAPDH mRNA expression at baseline, 12 hours and 48 hours after LAD ligation from a representative animal.
- D. Time-dependent measurement of rat IL-8/Gro-alpha protein in serum of rats undergoing LAD ligation. Migration of CD34+ human bone marrow-derived cells to ischemic rat myocardium is inhibited by mAbs against either rat IL-8 or the IL-8/Gro chemokine family receptors CXCR1 and CXCR2 (all p<0.01), but not against VEGF or its receptor Flk-1 (results are expressed as mean±sem of three separate experiments).
- E. Co-administration of blocking mAbs against either IL-8 and Gro-alpha, or against the surface receptors for these pro-angiogenic chemokines, CXCR-1 and CXCR-2, reduced myocardial trafficking of human angioblasts by 40-60% relative to control antibodies (p<0.01).

Figure 9:
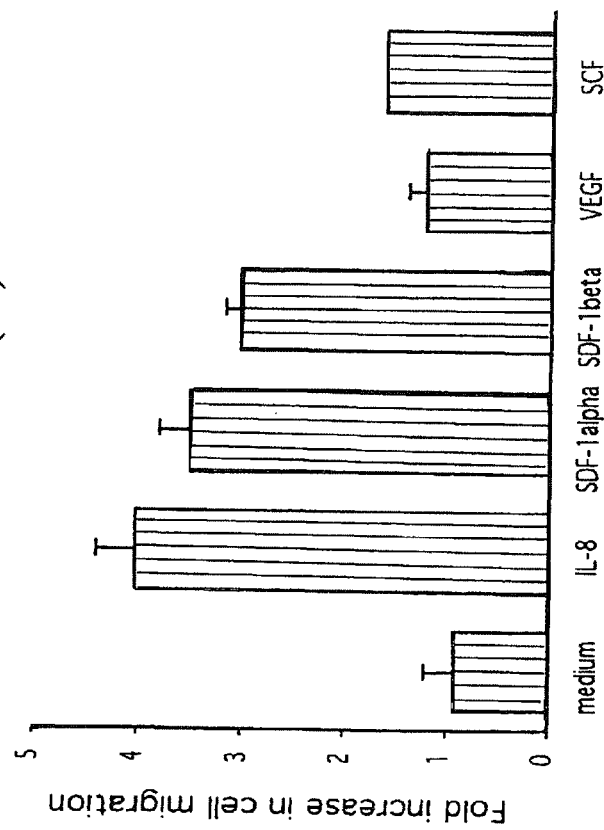
Figure 9:
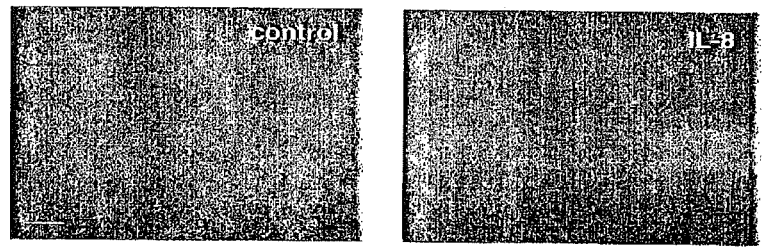

FIG. 9. CXC Chemokines Directly Induce Chemotaxis Of Bone Marrow-Derived Human CD34+ Cells To Rat Myocardium.

A and B depict results of in vitro chemotaxis of 98% pure human CD34+ cells to various conditions using a 48-well chemotaxis chamber (Neuro Probe, MD). Chemotaxis is defined as the number of migrating cells per high power field (hpf) after examination of 10 hpf per condition tested.
- A. IL-8 induces chemotaxis in a dose-dependent manner (results are expressed as mean±sem of three separate experiments).
- B. Chemotaxis is increased in response to IL-8 and SDF-1 alpha/beta, but not VEGF or SCF.
- C. Representative fluorescence microscopy demonstrating increased infiltration of intravenously-injected DiI-labeled human CD34+ cells (98% purity) into rat heart after intracardiac injection with IL-8 compared with saline injection.
- D. Intracardiac injection of IL-8 at 1 mg/ml significantly increases in vivo chemotaxis of DiI-labeled human CD34+ cells (98% purity) into rat heart in comparison with injection of saline, VEGF or stem cell factor (SCF), p<0.01 (results are expressed as mean±sem of three separate experiments).

Figure 10:
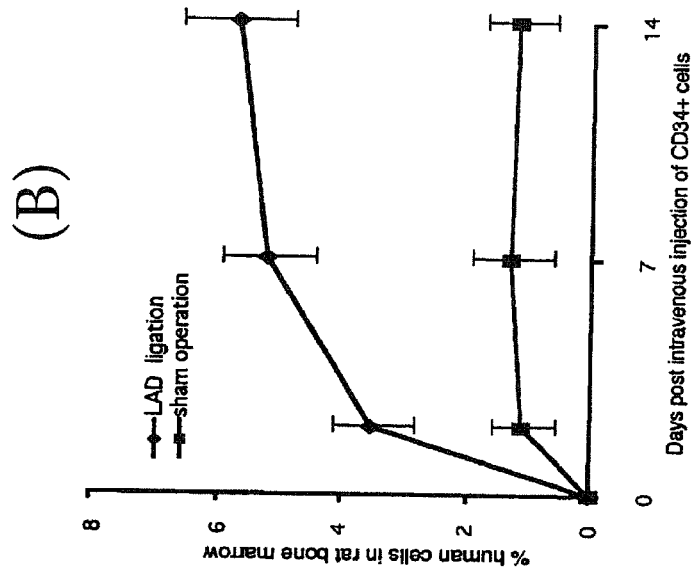

FIG. 10. Blocking CXCR4/SDF-1 Interactions Redirects Intravenously Injected Human CD34+ Angioblasts From Bone Marrow To Ischemic Myocardium.
- A. Depicted is the response of single-donor CD34-positive human cells cultured for 96 hours in RPMI with 20% normal rat serum, ischemic rat serum or 20 ng/ml VEGF. The numbers of CD117$^{bright}$GATA-2$^{pos}$ cells were quantitated by both [$^3$H] thymidine uptake and by flow cytometry. Ischemic serum induced a greater proliferative response of CD117$^{bright}$GATA-2$^{pos}$ cells compared with each of the other conditions (both p<0.01).
- B. The proportion of human CD34+ cells in rat bone marrow 2-14 days after intravenous injection is significantly increased after ischemia induced by LAD ligation (results are expressed as mean±sem of bone marrow studies in three animals at each time point).
- C,D. Effects of mAbs against CXCR4, SDF-1 or anti-CD34 on trafficking of human CD34+ cells to rat bone marrow and myocardium following LAD ligation. Co-administration of anti-CXCR4 or anti-SDF-1 significantly reduced trafficking of 98% pure CD34+ cells to rat bone marrow at 48 hours and increased trafficking to ischemic myocardium (results are expressed as mean±sem of bone marrow and cardiac studies performed in three LAD-ligated animals at 48 hours after injection).

Figure 11:
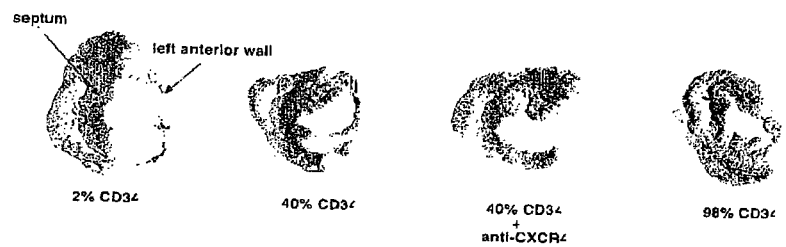

FIG. 11. Redirected Trafficking Of Human CD34+ Angioblasts To The Site Of Infarction Prevents Remodeling And Improves Myocardial Function.
- A,B. The effects of human CD34+ cells on reduction in LVAs (A) and improvement in LVEF (B) after myocardial infarction. Whereas injection of 2.0×10$^6$ human cells containing 98% CD34+ purity significantly improved LVEF and reduced LVAs (both p<0.01), injection of 2.0×10$^6$ human cells containing 2% and 40% CD34+ purity did not have any effect on these parameters in comparison to animals receiving saline. However, co-administration of anti-CXCR4 together with 40% pure CD34+ cells significantly improved LVEF and reduced LVAs (both p<0.01), to levels approaching use of cells with 98% purity.
- C. Sections of rat hearts stained with Masson's trichrome at 15 weeks after LAD ligation and injection of 2.0×10$^6$ human cells containing 2%, 40%, or 98% CD34+ purity. Hearts of rats receiving 2% and 40% pure CD34+ cells had greater loss of anterior wall mass, collagen deposition (blue), and septal hypertrophy compared with hearts of rats receiving 98% pure CD34+ cells. Co-administration of anti-CXCR4 mAb together with 40% pure CD34+ cells increased left ventricular wall mass and reduced collagen deposition.

D. Shows the mean proportion of scar/normal left ventricular myocardium in rats receiving >98% pure CD34+ cells or 40% pure CD34+ cells together with anti-CXCR4 mAb is significantly reduced in comparison to rats receiving 2% and 40% pure CD34+ cells (p<0.01) (results are expressed as mean±sem of three separate experiments).

Figure 12:
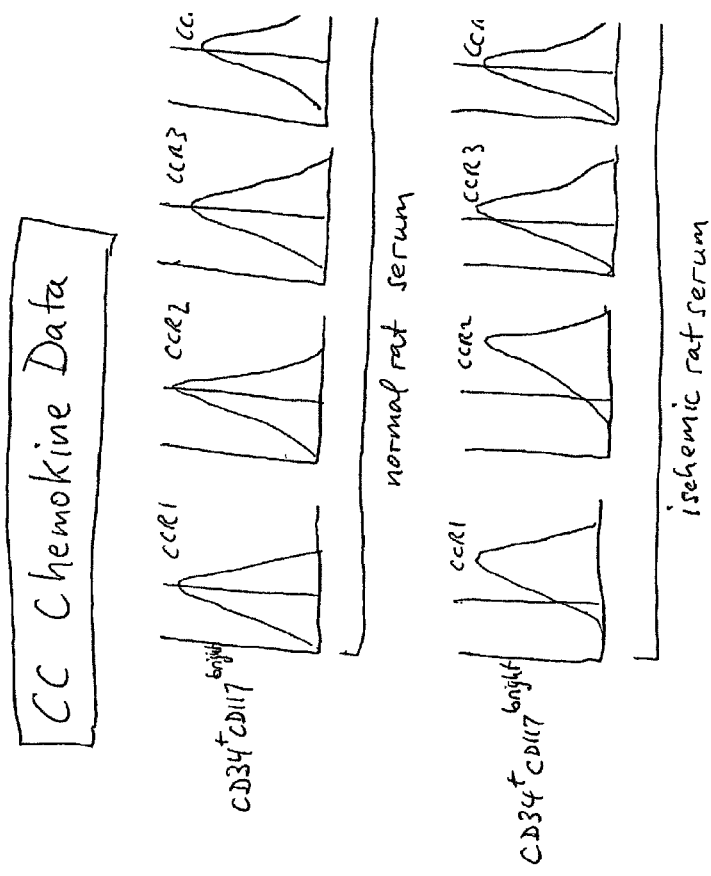

FIG. 12. Culture of CD34+CD117$^{bright}$ angioblasts with serum from LAD-ligated rats increases surface expression of CCR1 and CCR2, while surface expression of CCR3 and CCR5 remains unchanged.

Figure 13:
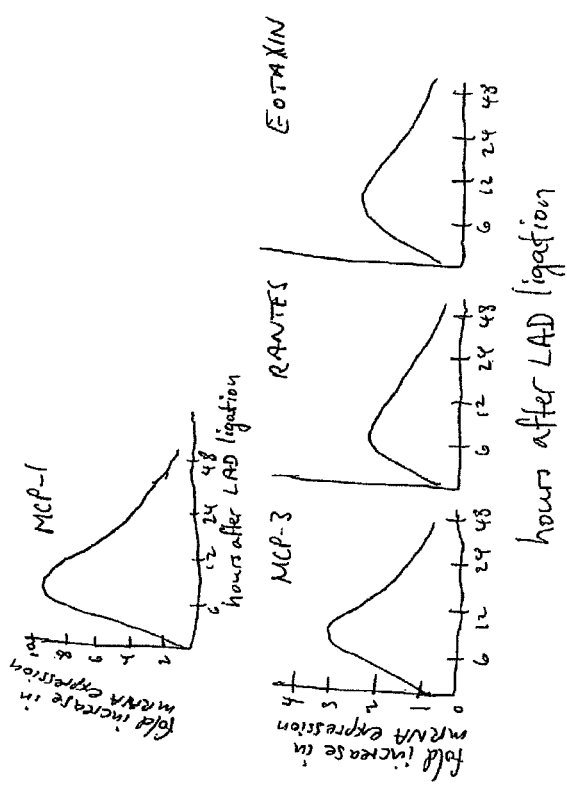

FIG. 13. Infarcted myocardium demonstrate a time-dependent increase in mRNA expression of several CCR-binding chemokines.

Figure 14:
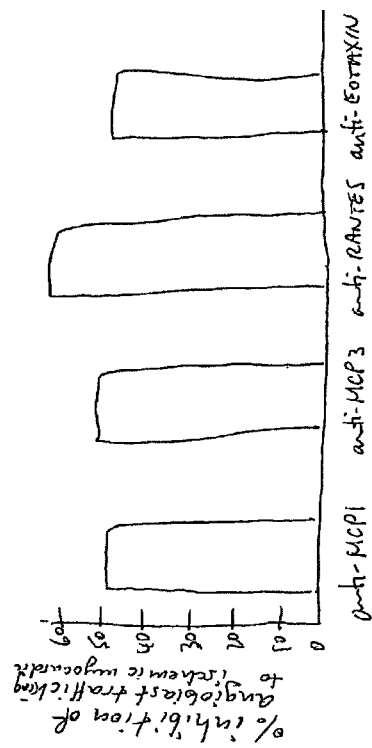

FIG. 14. Co-administration of blocking mAbs against MCP-1, MCP-3, and RANTES, or against eotaxin, reduced myocardial trafficking of human angioblasts by 40-60% relative to control antibodies (p<0.01).

Figure 15:
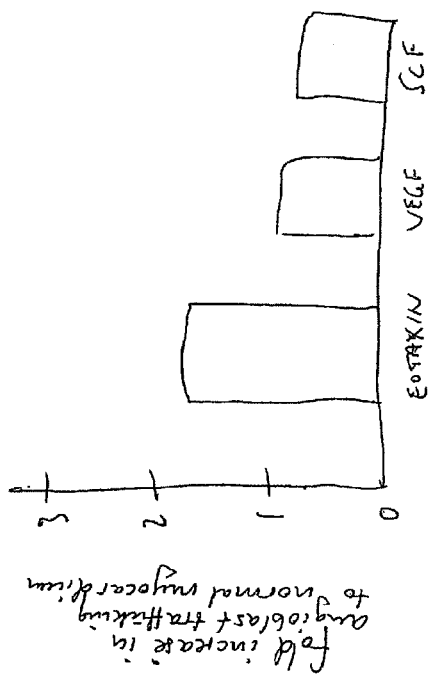

FIG. 15. Intracardiac injection of eotaxin into non-infarcted hearts induced 1.5-1.7 fold increase in CD34+ angioblast trafficking whereas injection of the growth factors VEGF and stem cell factor had no effect on chemotaxis despite increasing angioblast proliferation (not shown).

DETAILED DESCRIPTION OF THE INVENTION

As used herein, and unless stated otherwise, each of the following terms shall have the definition set forth below.

As used herein, "BMEC" is defined as bone marrow-derived endothelial cells.

As used herein, vasculogenesis is defined as the creation of new blood vessels from cells that are "pre-blood" cells such as bone marrow-derived endothelial cell precursors.

As used herein, mobilization is defined as inducing bone marrow-derived endothelial cell precursors to leave the bone marrow and enter the peripheral circulation. One of skill is aware that mobilized stem cells may be removed from the body by leukopheresis.

As used herein, ischemia is defined as inadequate blood supply (circulation) to a local area due to blockage of the blood vessels to the area.

As used herein, cytokine is defined as a factor that causes cells to grow or activate.

As used herein, chemokine is defined as a factor that causes cells to move to a different area within the body.

As used herein, ischemic heart disease is defined as any condition in which blood supply to the heart is decreased.

As used herein, "angiogenesis" is defined as the creation of blood vessels from pre-existing blood vessel cells.

As used herein, ischemic heart disease is defined as any condition in which blood supply to the heart is decreased.

As used herein, "VEGF" is defined as vascular endothelial growth factor. "VEGF-R" is defined as vascular endothelial growth factor receptor. "FGF" is defined as fibroblast growth factor. "IGF" is defined as Insulin-like growth factor. "SCF" is defined as stem cell factor. "G-CSF" is defined as granulocyte colony stimulating factor. "M-CSF" is defined as macrophage colony stimulating factor. "GM-CSF" is defined as granulocyte-macrophage colony stimulating factor. "MCP" is defined as monocyte chemoattractant protein.

As used herein, "CXC" chemokine refers to the structure of the chemokine. Each "C" represents a cysteine and "X" represents any amino acid.

As used herein, "CC" chemokine refers to the structure of the chemokine. Each "C" represents a cysteine.

As used herein, "recovered" means detecting and obtaining a cell based on the recoverable cell being a cell that binds a detectably labeled antibody directed against a specific marker on a cell including, but not limited to, CD117, GATA-2, GATA-3, and CD34.

As described herein, the chemokine administered to the subject could be in the protein form or nucleic acid form.

This invention provides a method of stimulating vasculogenesis in ischemia-damaged tissue of a subject comprising:
  (a) removing stem cells from a location within the subject;
  (b) recovering endothelial progenitor cells from the stem cells removed in step (a); and
  (c) introducing the endothelial progenitor cells from step (b) into a different location within the subject such that the endothelial progenitor cells stimulate vasculogenesis in the subject's ischemia-damaged tissue.

In a further embodiment the endothelial progenitors are frozen for a period of time in between steps (b) and (c). In one embodiment the ischemia-damaged tissue is myocardium. In another embodiment the ischemia-damaged tissue is nervous system tissue.

In one embodiment the endothelial progenitors are expanded by contacting the endothelial progenitors with a growth factor subsequent to step (b), but before step (c). In a further embodiment the growth factor is a cytokine. In further embodiments the cytokine is VEGF, FGF, G-CSF, IGF, M-CSF, or GM-CSF. In another embodiment the growth factor is a chemokine. In a further embodiment the chemokine is Interleukin-8. In one embodiment the endothelial progenitors are separated from other stem cells before expansion. In a further embodiment the endothelial progenitors are frozen for a period of time after expansion but before step (c).

In one embodiment step (a) occurs prior to the subject suffering ischemia-damaged tissue and wherein step (c) occurs after the subject has suffered ischemia-damaged tissue.

In one embodiment the stem cells are removed directly from the subject's bone marrow. In a further embodiment the stem cells are removed by aspiration from the subject's bone marrow. In one embodiment the stem cells are removed from the subject by a method comprising:
  a) introducing a growth factor into the subject to mobilize the stem cells into the subject's blood; and
  b) subsequently removing a sample of blood containing stem cells from the subject.

In a further embodiment the growth factor is introduced subcutaneously, orally, intravenously or intramuscularly. In one embodiment the growth factor is a chemokine that induces mobilization. In a further embodiment the chemokine is Interleukin-8. In one embodiment the growth factor is a cytokine. In a further embodiment the cytokine is G-CSF, M-CSF, or GM-CSF.

This invention also provides the instant method, wherein the endothelial progenitor cells are recovered based upon their expression of CD117.

This invention also provides the instant method, wherein the endothelial progenitor cells are recovered based upon their expression of a GATA-2 activated gene product. In one embodiment the gene product is selected from the following group: preproendothelin-1, big endothelin, endothelin-1.

In one embodiment the endothelial progenitors express GATA-2, and the endothelial progenitors are recovered as such by detection of intracellular GATA-2 expression or GATA-2 activity in those cells.

In one embodiment the subject has suffered or is suffering from one or more of the following: myocardial infarction, chronic heart failure, ischemic heart disease, coronary artery disease, diabetic heart disease, hemorrhagic stroke, thrombotic stroke, embolic stroke, limb ischemia or another disease in which tissue is rendered ischemic.

In one embodiment the endothelial progenitors are introduced into the subject by injection directly into the peripheral circulation, heart muscle, left ventricle, right ventricle, coronary artery, cerebro-spinal fluid, neural tissue, ischemic tissue or post-ischemic tissue.

In one embodiment the method further comprises administering to the subject one or more of the following: an inhibitor of Plasminogen Activator Inhibitor, Angiotensin Converting Enzyme Inhibitor or a beta blocker, wherein such administration occurs prior to, concomitant with, or following step (c).

This invention also provides a method of stimulating angiogenesis in peri-infarct tissue in a subject comprising:
(a) removing stem cells from a location within a subject;
(b) recovering endothelial progenitor cells from the stem cells removed in step (a);
(c) expanding the endothelial progenitor cells recovered in step (b) by contacting the progenitor cells with a growth factor; and
(d) introducing the expanded endothelial progenitor cells from step (c) into a different location in the subject such that the endothelial progenitor cells stimulate angiogenesis in peri-infarct tissue in the subject.

This invention also provides a method of selectively increasing the trafficking of endothelial progenitor cells to ischemia-damaged tissue in a subject comprising:
(a) administering endothelial progenitor cells to a subject; and
(b) administering a chemokine to the subject so as to thereby attract the endothelial progenitor cells to the ischemia-damaged tissue.

In one embodiment the chemokine is administered to the subject prior to administering the endothelial progenitors. In an alternative embodiment the chemokine is administered to the subject concurrently with the endothelial progenitors. In an alternative embodiment the chemokine is administered to the subject after administering the endothelial progenitors. In one embodiment the chemokine is a CXC chemokine. In a further embodiment the CXC chemokine is selected from the group consisting of Interleukin-8, Gro-Alpha, or Stromal-Derived Factor-1. In one embodiment the chemokine is a CC chemokine. In a further embodiment the CC chemokine is selected from the group consisting of RANTES, EOTAXIN, MCP-1, MCP-2, MCP-3, or MCP-4.

In one embodiment the chemokine is administered to the subject by injection into peripheral circulation, heart muscle, left ventricle, right ventricle, coronary arteries, cerebro-spinal fluid, neural tissue, ischemic tissue or post-ischemic tissue.

This invention also provides a method of increasing trafficking of endothelial progenitor cells to ischemia-damaged tissue in a subject comprising inhibiting any interaction between Stromal-Derived Factor-1 and CXCR4.

In one embodiment the interaction between Stromal-Derived Factor-1 (SDF-1) and CXCR4 is inhibited by administration of an anti-SDF-1 or an anti-CXCR4 monoclonal antibody to the subject. In one embodiment the instant method further comprises administering to the subject ACE inhibitor, AT-receptor blocker, or beta blocker. ng enzyme inhibitor, an AT$_1$-receptor blocker, or a beta blocker.

This invention also provides a method of reducing trafficking of endothelial progenitor cells to bone marrow in a subject comprising inhibiting production of Stromal-Derived Factor-1 in the subject's bone marrow. In one embodiment the SDF-1 production is inhibited by administration of an anti-SDF-1 or anti-CXCR4 monoclonal antibody to the subject.

This invention also provides a method for treating a cancer in a subject comprising administering to the subject a monoclonal antibody directed against an epitope of a specific chemokine produced by proliferating cells associated with the cancer so as to reduce, trafficking of endothelial progenitor cells to such proliferating cells and thereby treat the cancer in the subject.

This invention also provides a method for treating a cancer in a subject comprising administering to the subject a monoclonal antibody directed against an epitope of a specific receptor located on an endothelial progenitor cell, for a chemokine produced by proliferating cells associated with the cancer, so as to reduce trafficking of the endothelial progenitor cell to such proliferating cells and thereby treat the cancer in the subject.

This invention also provides a method for treating a tumor in a subject comprising administering to the subject an antagonist to a specific receptor on an endothelial progenitor cell so as to reduce the progenitor cell's ability to induce vasculogenesis in the subject's tumor and thereby treat the tumor.

This invention also provides a method for treating a tumor in a subject comprising administering to the subject an antagonist to a specific receptor on an endothelial progenitor cell so as to reduce the progenitor cell's ability to induce angiogenesis in the subject's tumor and thereby treat the tumor.

This invention also provides a method for expressing a gene of interest in an endothelial progenitor cell or a mast progenitor cell which comprises inserting into the cell a vector comprising a promoter containing a GATA-2 motif and the gene of interest.

This invention also provides the instant method, wherein the vector is inserted into the cell by transfection.

This invention also provides the instant method, wherein the promoter is a preproendothelin-1 promoter.

This invention also provides the instant method, wherein the promoter is of mammalian origin.

This invention also provides the instant method, wherein the promoter is of human origin.

This invention provides a composition comprising an amount of a monoclonal antibody directed against an epitope of a specific chemokine produced by a cancer effective to reduce trafficking of endothelial progenitor cells to the cancer, and a pharmaceutically acceptable carrier.

This invention provides a method of treating an abnormality in a subject wherein the abnormality is treated by the expression of a GATA-2 activated gene product in the subject comprising:
(a) removing stem cells from a location within the subject;
(b) recovering endothelial progenitor cells from the stem cells removed in step (a);
(c) recovering those endothelial progenitor cells recovered in step (b) that express GATA-2;
(d) inducing the cells recovered in step (c) as expressing GATA-2 to express a GATA-2 activated gene product; and
(e) introducing the cells expressing a GATA-2 activated gene product from step (d) into a different location in the subject such as to treat the abnormality.

In one embodiment the abnormality is ischemia-damaged tissue. In one embodiment the gene product is proendothelin. In one embodiment the gene product is endothelin. In one embodiment the subject is a mammal. In a further embodiment the mammal is a human This invention provides a method of treating an abnormality in a subject wherein the abnormality is treated by the expression of a GATA-2 activated gene product in the subject comprising:
 (a) removing stem cells from a location within the subject;
 (b) recovering mast progenitor cells from the stem cells removed in step (a);
 (c) recovering those mast progenitor cells recovered in step (b) that express GATA-2;
 (d) inducing the cells recovered in step (c) as expressing GATA-2 to express a GATA-2 activated gene product; and
 (e) introducing the cells expressing a GATA-2 activated gene product from step (d) into a different location in the subject such as to treat the abnormality In one embodiment the abnormality is ischemia-damaged tissue. In one embodiment the gene product is proendothelin. In one embodiment the gene product is endothelin. In one embodiment the subject is a mammal. In a further embodiment the mammal is a human.

This invention provides the a method of improving myocardial function in a subject that has suffered a myocardial infarct comprising:
 (a) removing stem cells from a location in the subject;
 (b) recovering cells that express CD117 from the stem cells; and
 (c) introducing the recovered cells into a different location in the subject such that the cells improve myocardial function in the subject.

In one embodiment the subject is a mammal. In a further embodiment the mammal is a human.

This invention also provides a method of stimulating vasculogenesis in ischemia-damaged tissue in a subject comprising:
 (a) obtaining allogeneic stem cells;
 (b) recovering endothelial progenitor cells from the stem cells removed in step (a); and
 (c) introducing the endothelial progenitor cells recovered in step (b) into the subject such that the endothelial progenitor cells stimulate vasculogenesis in the subject's ischemia-damaged tissue.

In alternative embodiments the allogeneic stem cells are removed from embryonic, fetal or cord blood sources.

This invention provides a method of stimulating angiogenesis in ischemia-damaged tissue in a subject comprising:
 (a) obtaining allogeneic stem cells;
 (b) recovering endothelial progenitor cells in the stem cells removed in step (a); and
 (c) introducing the endothelial progenitor cells recovered in step (b) into the subject such that the endothelial progenitor cells stimulate angiogenesis in the subject's ischemia-damaged tissue.

In alternative embodiments the allogeneic stem cells are removed from embryonic, fetal or cord blood sources.

This invention also provides a method of improving myocardial function in a subject that has suffered a myocardial infarct comprising injecting G-CSF into the subject in order to mobilize endothelial progenitor cells.

This invention also provides a method of improving myocardial function in a subject that has suffered a myocardial infarct comprising injecting anti-CXCR4 antibody into the subject. In one embodiment the method further comprises introducing endothelial progenitors into the subject. In one embodiment the method further comprises introducing G-CSF into the subject in order to mobilize endothelial progenitors.

The present invention provides a method of selectively increasing the trafficking of human, bone marrow-derived endothelial cell precursors to the site of tissue damaged by ischemic injury which comprises administering chemokines to the subject so as to thereby attract endothelial cell precursors to the ischemic tissue. In an embodiment of this invention the ischemic tissue is myocardium. In an embodiment of this invention the ischemic tissue is neural tissue. In an embodiment of this invention the chemokine is administered to the subject by injection into peripheral circulation, heart muscle, left ventricle, right ventricle, coronary arteries, spinal fluid, neural tissue, or other site of ischemia. In an embodiment of this invention the chemokine is a CXC chemokine. In an embodiment of this invention the CXC chemokine is selected from the group consisting of Interleukin-8 (IL-8), Gro-Alpha, and Stromal Derived Factor-1 (SDF-1). In an embodiment of this invention the chemokine is a CC chemokine. In an embodiment of this invention the CC chemokine is selected from the group consisting of MCP-1, MCP-2, MCP-3, MCP-4, RANTES, and EOTAXIN.

This invention will be better understood by reference to the Experimental Details which follow, but those skilled in the art will readily appreciate that the specific experiments detailed are only illustrative of the invention as described more fully in the claims which follow thereafter.

EXPERIMENTAL DETAILS

First Series of Experiments

Figure 1:
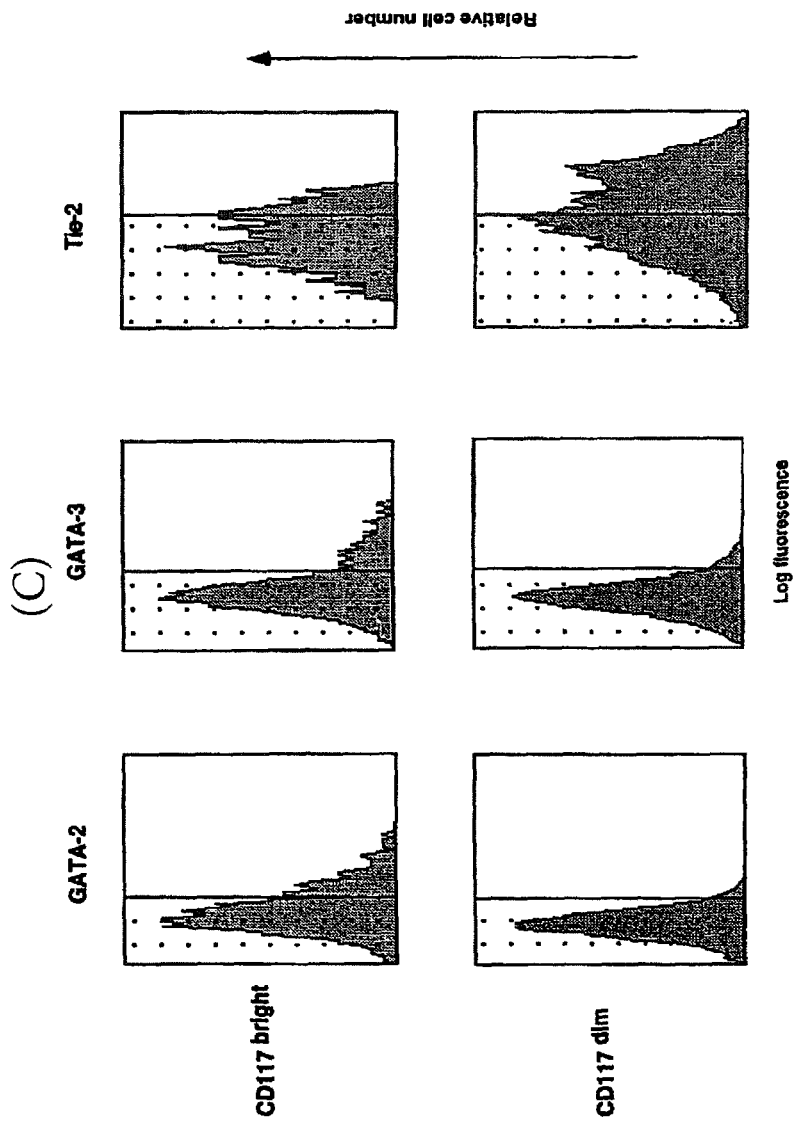
FIG. 1. G-CSF Mobilizes Two Human Bone Marrow-Derived Populations Expressing VEGF Receptors: One With Characteristics Of Mature Endothelial Cells And A Second With Characteristics Of Embryonic Angioblasts.
Figure 1:
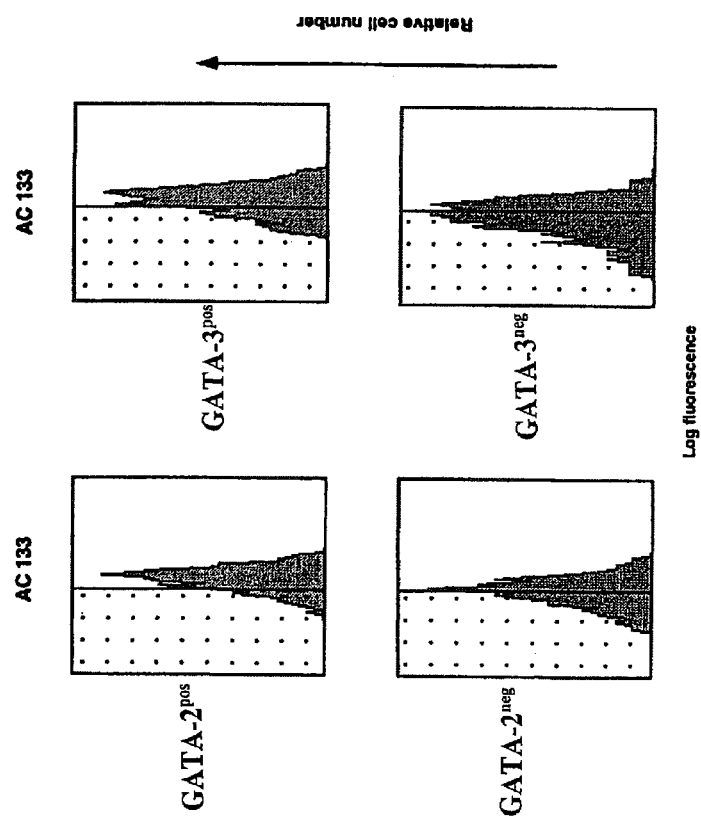

Experimental Procedures and Results
1. Mobilization and Identification of Bone Marrow-Derived Cells Following G-CSF mobilization, 60-80% of highly purified human CD34 cells (>90% positive) co-expressed the stem cell factor receptor CD117, FIG. 1a, of which 15-25% expressed CD117 brightly and 75-85% expressed CD117 dimly. By quadruple parameter analysis, two populations of CD34 cells were recovered which expressed VEGFR-2 (Flk-1), one accounting for 20-30% of $CD117^{dim}$ cells and expressing high levels of VEGFR-2, and a second accounting for 10-15% of $CD117^{bright}$ cells and expressing lower levels of vEGFR-2, FIG. 1b. The VEGFR-2 positive cells within the CD34+$CD117^{dim}$ population, but not those within the CD34+$CD117^{bright}$ subset, displayed phenotypic characteristics of mature, vascular endothelium, including high level expression of Tie-2, ecNOS, vWF, E-selectin (CD62E), and SCAM (CD54). In contrast, as shown in FIG. 1c, the VEGFR-2 positive cells within the CD34+$CD117^{bright}$ subset, but not those within the CD34+$CD117^{dim}$ subset, expressed markers characteristic of primitive hemangioblasts arising during waves of murine and human embryogenesis, including GATA-2, GATA-3, and low levels of Tie-2. Moreover, $CD117^{bright}$ cells which co-expressed GATA-2 and GATA-3 were also strongly AC133 positive, another marker which has recently been suggested to define a hematopoietic population with angioblast potential (2), FIG. 1d. However, since AC133 expression was also detected on a subset of $CD117^{dim}$ cells which was negative for GATA-2 and GATA-3, we conclude that identification of an embryonic bone-marrow derived angioblast (BA) phenotype requires concomitant expression of GATA-2, GATA-3, and $CD117^{bright}$ in addition to AC133. Thus, G-CSF treatment mobilizes into the peripheral circulation a prominent population of mature, bone marrow-derived endothelial cells (BMEC), and a smaller bone marrow-derived population with phenotypic characteristics of embryonic angioblasts (BA).

2. Expansion of Bone Marrow-Derived Cells

Since the frequency of circulating endothelial cell precursors in animal models has been shown to be increased by either VEGF (27) or regional ischemia (10-13), we next compared the proliferative responses of BA and BMEC to VEGF and to factors in ischemic serum (28). As shown in FIG. 2a, following culture for 96 hours with either VEGF or ischemic serum, $CD117^{bright}GATA-2^{pos}$ BA demonstrated significantly higher proliferative responses relative to $CD117^{dim}GATA-2^{neg}$ BMEC from the same donor. For VEGF, BA showed 2.9-fold increase in proliferation above baseline compared with 1.2-fold increase for BMEC, p<0.01, while for ischemic serum from Lew rate with myocardial infarction BA showed 4.3-fold increase in proliferation above normal serum compared with 1.7-fold increase for BMEC, p<0.01. Culture with either VEGF or ischemic serum greatly expanded the BA population of large blast cells, FIG. 2b, which continued to express immature markers, including GATA-2, GATA-3, and $CD117^{bright}$, but not markers of mature endothelial cells, FIG. 2c, indicating blast proliferation without differentiation. Following culture of CD34-positive monolayers on fibronectin in endothelial growth medium for 7 days (29), an exuberant cobblestone pattern of proliferation was seen, FIG. 3a, with the majority of the adherent monolayers (>95%) having features characteristic of endothelial cells, FIG. 3b-e, including uniform uptake of acetylated LDL, and co-expression of CD34, factor VIII, and eNOS. Since the BMEC population had low proliferative responses to VEGF or cytokines in ischemic serum, the origin of the exuberant endothelial cell outgrowth in culture is most likely the BA population defined by surface expression for GATA-2, GATA-3, and $CD117^{bright}$.

Figures 4A, 4B, 4C, 4D:
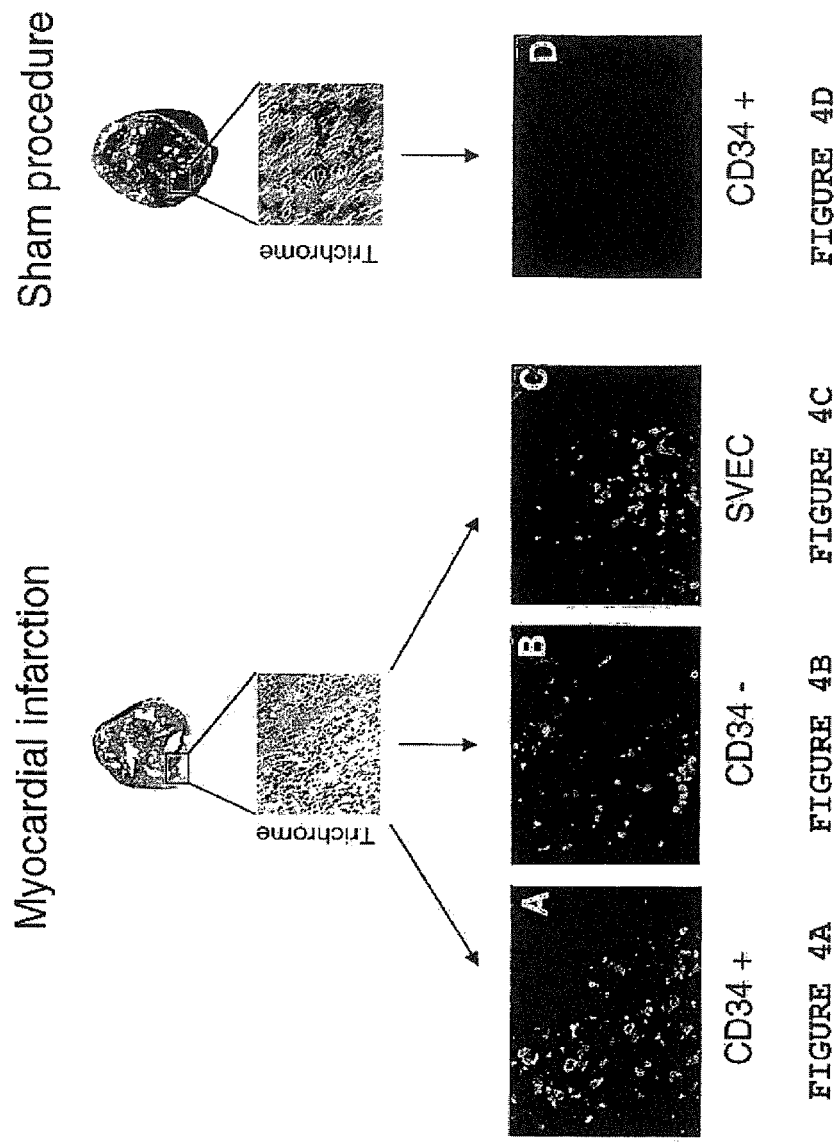
Figure 4F:

3. In Vivo Migration of Bone Marrow-Derived CD34+ Cells to Sites of Regional Ischemia Next we compared the in vivo migratory and proliferative characteristics of bone marrow- and peripheral vasculature-derived human cells after induction of regional ischemia. As shown in FIG. 4a-c, intravenous injection of $2\times10^6$ DiI-labeled human CD34-positive cells (>95% CD34 purity), CD34-negative cells (<5% CD34 purity), or saphenous vein endothelial cells (SVEC), into nude rats after coronary artery ligation and infarction resulted in similar degree of infiltration in rat myocardium at 48 hours (30) The trafficking was specifically directed to the infarct area since few DiI-labeled cells were detected in unaffected areas of hearts with regional infarcts, not shown, and neither G-CSF mobilized CD34+ cells nor mature human endothelial cells infiltrated normal myocardium, FIG. 4d. Although similar numbers of CD34+ and CD34– cells migrated to ischemic myocardium, the proportional increase in human GATA-2 mRNA expression in ischemic myocardium relative to normal myocardium (31) was 2.6-fold greater following injection of highly CD34-enriched cells compared with CD34-cells (p<0.001), FIG. 4e. Moreover, blood vessels which incorporated human endothelial cells, as defined by co-expression of DiI, HLA class I, and factor VII, could be detected two weeks after injection of human CD34+ cells, but not after injection of CD34– cells or SVEc, FIG. 4f. Together, these results indicate that adult bone marrow-derived human CD34+ cells contain a population which selectively responds to in vivo signals from sites of regional ischemia with augmented migration, localization, and endothelial differentiation.

4. Effects of Injection of G-CSF Mobilized Human CD34+ Cells into Infarcted Rat Myocardium We next compared the functional effects of injecting G-CSF mobilized human CD34+(>95%) cells, CD34– (<5%) cells, peripheral saphenous vein cells, or saline, into infarcted rat myocardium. After LAD ligation, left ventricular function was severely depressed in each group of recipients, with left ventricular ejection fraction (LVEF) being reduced by means of 25-43% and left ventricular end-systolic area being increased by means of 44-90%, FIGS. 5 a and b. Remarkably, within two weeks of injecting G-CSF mobilized adult human CD34+ cells, LVEF recovered by a mean of 22±6% (p<0.001), FIG. 5a. This effect was long-lived, and increased by the end of follow-up, 15 weeks, to 34±4%. In contrast, injection of G-CSF mobilized human CD34– cells, saphenous vein endothelial cells, or saline, had no effect on LVEF. In a parallel fashion, injection of G-CSF mobilized human CD34+ cells reduced left ventricular end-systolic area by a mean of 26±8% by 2 weeks and 37±6% by 15 weeks, whereas none of the other recipient groups demonstrated such effect (p<0.001), FIG. 5b. Representative echocardiographic examples for each group are shown in FIG. 5c. Moreover, at 15 weeks post-infarction mean cardiac index in rats injected with CD34+ cells was only reduced by 26±8% relative to normal rats, whereas mean cardiac index for each of the other groups was reduced by 48-59% (p<0.001), FIG. 5d.

Histologic examination at two weeks post-infarction (33) revealed that injection of CD34+ cells was accompanied by significant increase in microvascularity and cellularity of granulation tissue, and decrease in matrix deposition and fibrosis within the infarct zone in comparison to controls, FIGS. 6 a and b. Moreover, ischemic myocardium of rats injected with human CD34+ cells contained significantly greater numbers of factor VIII-positive interstitial angioblasts and capillaries in comparison to ischemic myocardium of control rats, FIGS. 6 c and d.

Quantitation of capillary numbers demonstrated a significant increase in neo-angiogenesis within the infarct zone of rats who received CD34+ cells (mean number of factor VIII-positive capillaries per high power field 92±5 vs 51±4 in saline controls, p<0.01), but not within normal myocardium (36±2 vs 37±3 capillaries per high power field). No increase in capillary numbers were observed in ischemic rat myocardium infiltrated with CD34– cells or SVEC. At 15 weeks post-infarction, rats receiving highly purified CD34+ cells demonstrated significantly reduced infarct zone sizes together with increased mass of viable myocardium within the anterior free wall compared to each of the other groups, FIGS. 6e and f. Numerous vessels were evident at the junction of the infarct zone and viable myocardium in tissues infiltrated with CD34+ cells. Whereas collagen deposition and scar formation extended almost through the entire left ventricular wall thickness in controls, with aneurysmal dilatation and typical EKG abnormalities, the infarct scar extended only to 20-50% of the left ventricular wall thickness in rats receiving CD34+ cells. Moreover, pathological collagen deposition in the non-infarct zone was markedly reduced in rats receiving CD34+ cells. Overall, the mean proportion of scar/normal left ventricular myocardium was 13% in rats receiving CD34+ cells compared with 36-45% for each of the other groups (p<0.01), FIG. 6g.

Discussion

The experiments described above demonstrate that neo-angiogenesis of the infarct bed by human bone marrow-derived endothelial cell precursors prevents scar development, maintains viable myocardium, and improves ventricular function in a rodent model of myocardial ischemia. Following infarction, the viable myocardial tissue bordering the infarct zone undergoes a significant degree of hypertrophy (5,34-35). Although neoangiogenesis within the infarcted tissue appears to be an integral component of the remodeling process (36,37), under normal circumstances the capillary network cannot keep pace with tissue growth and is unable to support the greater demands of the hypertrophied, but viable, myocardium which subsequently undergoes apoptosis due to inadequate oxygenation and nutrient supply. The development of neoangiogenesis within the myocardial infarct scar appears to require activation of latent collagenase and other proteinases following plasminogen activation by urokinase-type plasminogen activator (u-PA) expressed on infiltrating leukocytes (38). The importance of bone marrow-derived endothelial precursors in this process has been demonstrated in u-PA −/− mice where transplantation of bone marrow from cogenic wild-type strains restored defective myocardial revascularization post-infarction (38). Since u-PA mRNA transcription and proteolytic activity in human mononuclear cells and tumor cell lines is significantly increased by the colony stimulating factors G-CSF, M-CSF, and GM-CSF (39-41), this provides a rationale for in vivo or ex vivo use of these cytokines to mobilize and differentiate large numbers of human adult bone marrow-derived angioblasts for therapeutic revascularization of the infarct zone.

Cell surface and RNA expression of the transcription factor GATA-2 appears to selectively identify human adult bone marrow-derived angioblasts capable of responding to signals from ischemic sties by proliferating and migrating to the infarct zone, and subsequently participating in the process of neo-angiogenesis. Of particular interest, GATA-2 is a co-factor for endothelial cell transcription of preproendothelin-1 (ppET-1) (42), the precursor molecule of the potent vasoconstrictor and hypertrophic autocrine peptide ET-1. Since ppET-1 transcription is also increased by angiotensin II (43), produced as a result of activation of the renin-angiotensin neurohormonal axis following myocardial infarction, the angioblasts infiltrating the infarct bed may be secreting high levels of ET-1 due to the synergistinc actions of angiotensin II surface receptor signalling and GATA-2 transactivation. The observation that newly-formed vessels within the infarct scar have thicker walls, lower vasodilator responses to stronger vasoactive substances than vessels within normal myocardium (44) are consistent with effects of increased autocrine ET-1 activity, and support the possibility that neo-angiogenic vasculature is derived from infiltrating GATA-2 positive angioblasts.

Together, the results of the above-described experiments indicate that injection of G-CSF mobilized adult human CD34+ cells with phenotypic and functional properties of embryonic hemangioblasts can stimulate neo-angiogenesis in the infarct vascular bed, thus reducing collagen deposition and scar formation in myocardial infarction. Although the degree of reduction in myocardial remodeling as a result of neoangiogenesis was striking, further augmentation in myocardial function might be achieved by combining infusion of human angioblasts with ACE inhibition or $AT_1$-receptor blockade to reduce angiotensin II-dependent cardiac fibroblast proliferation, collagen secretion, and plasminogen activator-inhibitor (PAI) production (45, 46). The use of cytokine-mobilized autologous human bone-marrow angioblasts for revascularization of myocardial infarct tissue, in conjunction with currently used therapies (47-49), offers the potential to significantly reduce morbidity and mortality associated with left ventricular remodeling post-myocardial infarction.

Second Series of Experiments

Methods
1. Purification of Cytokine-Mobilized Human CD34+ Cells

Single-donor leukopheresis products were removed from humans treated with recombinant G-CSF 10 mg/kg (Amgen, Calif.) sc daily for four days. Mononuclear cells were separated by Ficoll-Hypague, and highly-purified CD34+ cells (>98% positive) were removed using magnetic beads coated with anti-CD34 monoclonal antibody (mAb) (Miltenyi Biotech Ltd, CA). Purified CD34 cells were stained with fluorescein-conjugated mAbs against CD34, CD117, VEGFR-2, Tie-2, GATA-2, GATA-3, AC133, vWF, eNOS, CD54, CD62E, CXCR1, CXCR2, CXCR4, and analyzed by four-parameter fluorescence using FACScan (Becton Dickinson, Calif.).

2. Proliferative Studies of Human Endothelial Progenitors

Single-donor CD34-positive cells were cultured for 96 hours in RPMI with either 20% normal rat serum, ischemic rat serum or 20 ng/ml VEGF, then pulsed with [$^3$H] thymidine (Amersham Life Science Inc, IL, USA) (1 mlCi/well) and uptake was measured in an LK Betaplate liquid scintillation counter (Wallace, Inc., Gaithersburg, Md.). The proportion of $CD117^{bright}GATA-2^{pos}$ cells after 96 hours of culture in each condition was also quantitated by flow cytometry.

3. Chemotaxis of Human Hone Marrow-Derived Endothelial Progenitors

Highly-Purified CD34+ Cells (>98% Positive) were Plated in 48-well chemotaxis chambers fitted with membranes (8 mm pores) (Neuro Probe, MD). After incubation for 2 hours at 37°, chambers were inverted and cells were cultured for 3 hours in medium containing IL-8 at 0.2, 1.0 and 5.0 mg/ml, SDF-1 alpha/beta 1.0 mg/ml, VEGF and SCF. The membranes were fixed with methanol and stained with Leukostat (Fischer Scientific, Ill). Chemotaxis was calculated by counting migrating cells in 10 high-power fields.

4. Animals, Surgical Procedures, Injection of Human Cells, and Quantitation of Cellular Migration into Tissues Rowett (rnu/rnu) athymic nude rats (Harlan Sprague Dawley, Indianapolis, Ind.) were used in studies approved by the "Columbia University Institute for Animal Care and Use Committee". After anesthesia, a left thoracotomy was performed, the pericardium was opened, and the left anterior descending (LAD) coronary artery was ligated. Sham-operated rats had a similar surgical procedure without having a suture placed around the coronary artery. 48 hours after LAD ligation $2.0 \times 10^6$ DiI-labeled human CD34+ cells (>95%, 40%, <2% purity) removed from a single donor after G-CSF mobilization were injected into the tail vein in the presence or absence of mAbs with known inhibitory activity against CXCR1, CXCR2, CXCR4, CD34, rat IL-8 (ImmunoLaboratories, Japan) and rat SDF-1® & D Systems, MN), or isotype control antibodies. Control animals received saline after LAD ligation. Each group consisted of 6-10 rats. Quantitation of myocardial infiltration after injection of human cells was performed by assessment of DiI fluorescence in hearts from rats sacrificed 2 days after injection (expressed as number of DiI-positive cells per high power field, minimum 5 fields examined per sample). Quantitation of rat bone marrow infiltration by human cells was performed in 12 rats at baseline, days 2, 7, and 14 by flow cytometric and RT-PCR analysis of the proportion of HLA class I-positive cells relative to the total rat bone marrow population.

5. Analyses of Myocardial Function

Echocardiographic studies were performed at baseline, 48 hours after LAD ligation, and at 2, 6 and 15 weeks after injection of cells or saline, using a high frequency liner array transducer (SONOS 5500, Hewlett Packard, Andover, Mass.). 2D images were removed at mid-papillary and apical levels. End-diastolic (EDV) and end-systolic (ESV) left ventricular volumes were removed by bi-plane area-length method, and % left ventricular ejection fraction (LVEF) was calculated as $[(EDV-ESV)/EDV] \times 100$. Left ventricular area at the end of systole (LVAs) was measured by echocardiography at the level of the mitral valve. LVEF recovery and reduction in LVAs were calculated as the mean improvement between the respective values for each at different time points after LAD ligation relative to pre-infarct values.

6. Histology and Immunohistochemistry

Histologic studies were performed on explanted rat hearts at 2 and 15 weeks after injection of human cells or saline. Following excision, left ventricles from each experimental animal were sliced at 10-15 transverse sections from apex to base. Representative sections were put into formalin for histological examination, stained freshly with anti-factor VIII mAb using immunoperoxidase technique to quantitate capillary density, or stained with Masson trichrome and mounted. The lengths of the infarcted surfaces, involving both epicardial and endocardial regions, were measured with a planimeter digital image analyzer and expressed as a percentage of the total ventricular circumference. Final infarct size was calculated as the average of all slices from each heart.

7. Measurement of Rat CXC Chemokine mRNA and Protein Expression

Poly(A)+mRNA was extracted by standard methods from the hearts of 3 normal and 12 LAD-ligated rats. RT-PCR was used to quantify myocardial expression of rat IL-8 and Gro-alpha mRNA at baseline and at 6, 12, 24 and 48 hours after LAD ligation after normalizing for total rat RNA as measured by GAPDH expression. After priming with oligo (dT) 15-mer and random hexamers, and reverse transcribed with Monoley murine lymphotrophic virus reverse transcriptase (Invitrogen, Carlsbad, Calif., USA), cDNA was amplified in the polymerase chain reaction (PCR) using Taq polymerase (Invitrogen, Carlsbad, Calif., USA), radiolabeled dideoxynucleotide ([$\alpha^{32}$P]-ddATP: 3,000 Ci/mmol, Amersham, Arlington Heights, Ill.), and primers for rat IL-8, Gro-alpha and GAPDH (Fisher Genosys, CA). Primer pairs (sense/antisense) for rat IL-8, Gro-alpha AND GAPDH were, gaagatagattgcaccgatg (SEQ ID NO:1)/catagcctctcacatttc (SEQ ID NO:2), gcgcccgtccgccaatgagctgcgc (SEQ ID NO:3)/cttggggacacccttcagcatcttttgg (SEQ ID NO:4), and ctctacccacggcaagttcaa (SEQ ID NO:5)/gggatgaccttgcccacagc (SEQ ID NO:6), respectively. The labeled samples were loaded into 2% agarose gels, separated by electrophoresis, and exposed for radiography for 6 h at −70°. Serum levels of rat IL-8/Gro-alpha were measured at baseline and at 6, 12, 24 and 48 hours after LAD ligation in four rats by a commercial ELISA using polyclonal antibodies against the rat IL-8/Gro homologue CINC (ImmunoLaboratories, Japan). The amount of protein in each serum sample was calculated according to a standard curve of optical density (OD) values constructed for known levels of rat IL-8/Gro-alpha protein.

Experimental Procedures and Results

1. Selective Trafficking of Endothelial Precursors

Following immunoselection of G-CSF mobilized human CD34 cells to >98% purity, 60-80% co-expressed the stem cell factor receptor CD117. By quadruple parameter analysis, FIG. 7a, 10-15% of CD117$^{bright}$ cells were found to express a phenotype characteristic of embryonic angioblasts, with low level surface expression of VEGFR-2 and Tie-2, as well as the transcription factors GATA-2 and GATA-3, and AC133, recently shown to identify endothelial precursors (79). These cells did not express markers of mature endothelial cells such as vWF, eNOS and E-selectin, but were positive for the CXC chemokine receptors 1, 2, and 4. Intravenous injection of $2\times10^6$ DiI-labeled human CD34+ cells (>98%, 40%, and 2% purity into LAD-ligated Rowett nude rats was accompanied at 48 hours by dense infiltration of rat myocardium, FIG. 7b. The trafficking of these cells was specifically directed to the infarct area since few DiI-labeled cells were detected in unaffected areas of hearts with regional infarcts, not shown, and DiI-labeled cells did not infiltrate myocardium from sham-operated rats, FIG. 7b. By two weeks post-injection, rats receiving >98% pure human CD34+ cells demonstrated increased infarct bed microvascularity and reduced matrix deposition and fibrosis, FIG. 7c. The number of factor VIII-positive capillaries per high power field was over three-fold higher in the infarct bed of rata receiving $2\times10^6$ cells containing >98% pure CD34+ purity than in the analogous region in rats receiving $2\times10^6$ cells containing either 2% or 40% CD34+ purity, p<0.01, FIG. 7c. Moreover, the majority of these capillaries were of human origin since they expressed HLA class I molecules (not shown). Thus, although various populations of human bone marrow-derived cells migrate to the infarct bed, vasculogenesis appears to require selective trafficking of a critical number of endothelial precursors.

2. Effects of Ischemia on CXC Chemokine Production by Infarcted Myocardium

Since human leukocyte chemotaxis and tissue infiltration is regulated by interactions between specific chemokines and CXC cell surface receptors, we next investigated the effects of ischemia on CXC chemokine production by infarcted rat myocardium. As shown in FIG. 8a-c, infarcted myocardium demonstrated a time-dependent increase in mRNA expression of the CXCR1/2-binding ELR-positive chemokines IL-8 and Gro-alpha, with maximal expression, at 6-12 hours after LAD ligation. In comparison to non-infarcted myocardium, tissues after LAD ligation expressed 7.2-7.5 fold higher mRNA levels of these ELR-positive pro-angiogenic chemokines after normalizing for total mRNA content (p<0.001). Moreover, serum IL-8 levels increased by 8-10 fold within 6-12 hours after LAD ligation (p<0.001), and remained elevated at 48 hours, FIG. 8d. Co-administration of blocking mAbs against either IL-8 and Gro-alpha, or against the surface receptors for these pro-angiogenic chemokines, CXCR1 or CXCR2, reduced myocardial trafficking of human angioblasts by 40-60% relative to control antibodies (p<0.01), FIG. 8e.

3. Chemotactic Responses of Human Bone Marrow-Derived CD34+ Angioblasts to Chemokines.

In subsequent experiments we directly measured in vitro and in vivo chemotactic responses of human bone marrow-derived CD34+ angioblasts to IL-8. As shown in FIG. 9a, in vitro chemotaxis of human CD34+ cells was induced by IL-8 in a dose-dependent manner, with concentrations between 0.2-5µ/ml. The ELR− chemokine SDF-1, produced constitutively by bone marrow stromal cells, induced a similar degree of chemotaxis of CD34+ cells at concentrations similar to IL-8, FIG. 9b. In contrast, chemotaxis was not induced by the growth factors VEGF or stem cell factor (SCF). Moreover, intracardiac injection of IL-8 at 1 µg/ml into non-infarcted hearts induced in vivo chemotaxis of CD34+ cells, FIG. 9c, whereas neither VEGF nor SCF, used as controls, had any chemotactic effect in vivo, FIG. 9d. Together, these results indicate that increased tissue expression of ELR-positive chemokines augments vasculogenesis in vivo by inducing chemotaxis of bone marrow-derived endothelial precursor cells to sites of tissue ischemia.

4. Interruption of CXCR4/SDF-1 Interactions to Redirect Trafficking of Human CD34-Positive Cells from Bone Marrow to Myocardium.

In addition to augmenting trafficking of intravenously injected human CD34+ angioblasts to damaged myocardium, ischemic serum from LAD-ligated rats caused rapid expansion of the circulating CD34+CD117$^{bright}$ angioblast population and concomitantly increased trafficking of these cells to the bone marrow. As shown in FIG. 10a, culture for 2 days with either VEGF or ischemic serum increased proliferation of CD34+CD117$^{bright}$ angioblasts by 2.8 and 4.3 fold, respectively (p<0.01). Moreover, as shown in FIG. 10b, bone marrow from ischemic rats after LAD ligation contained 5-8 fold higher levels of human CD34+CD117$^{bright}$ angioblasts compared with bone marrow from normal rats 2-14 days after intravenous injection of 2×10$^6$ human CD34-positive cells (>95% purity), (p<0.001). Since SDF-1 is constitutively expressed by bone marrow stromal cells and preferentially promotes bone marrow migration of circulating CD34+ cells which are actively cycling (80), we investigated whether the increased homing of human CD34+CD117$^{bright}$ angioblasts to ischemic rat bone marrow was due to heightened SDF-1/CXCR4 interactions. As shown in FIG. 10c, co-administration of mAbs against either human CXCR4 or rat SDF-1 significantly inhibited migration of intravenously administered CD34+ human angioblasts to ischemic rat bone marrow by compared with anti-CD34 control antibody (both p<0.001). Moreover, co-administration of mAbs against either human CXCR4 or rat SDF-1 increased trafficking of CD34+ human angioblasts to ischemic rat myocardium by a mean of 24% and 17%, respectively (both p<0.001), FIG. 10d. By two weeks, the myocardial infarct bed of rats receiving human CD34+ cells in conjunction with anti-CXCR4 mAb demonstrated >3-fold increase in microvascularity compared with those receiving CD34+ cells in conjunction with isotype control antibody. These results indicate that although intravenously injected CD34+ angioblasts traffick to infarcted myocardium and induce vasculogenesis in response to augmented production of ELR+ chemokines, the efficiency of this process is significantly reduced by concomitant angioblast migration to the bone marrow in response to SDF-1. Interruption of CXCR4/SDF-1 interactions redirects trafficking of the expanded, cycling population of human CD34-positive cells from bone marrow to myocardium after infarction, increasing infarct bed neoangiogenesis.

5. Improvement in Myocardial Function

Although left ventricular function was severely depressed after LAD ligation, injection of >98% pure CD34+ cells was associated with significant recovery in left ventricular size and function within two weeks, and these effects persisted for the entire 15 week period of follow-up, FIGS. 11 a and b. In rats receiving >98% pure CD34+ cells, left ventricular end-systolic area decreased by a mean of 37±6% by 15 weeks compared to immediately post-infarction, FIG. 11a, and left ventricular ejection fraction (LVEF) recovered by a mean of 34+4% by 15 weeks (p<0.001), FIG. 11b (p<0.001). Improvement in these parameters depended on the number of CD34+ cells injected, since intravenous injection of 2×10$^6$ G-CSF mobilized human cells containing 2% or 40% CD34+ purity did not significantly improve myocardial function despite similar degrees of trafficking to ischemic myocardium, FIGS. 11 a and b. However, co-administration of anti-CXCR4 mAb together with G-CSF mobilized human bone marrow-derived cells containing 40% CD34+ purity significantly improved LVEF recovery and reduced LVAs, to levels seen with >98% CD34+ purity. By trichrome stain, significant differences in left ventricular mass and collagen deposition were observed between the groups, FIG. 11c. In rats receiving 2×10$^6$ human cells containing 2% CD34 purity, the left ventricular anterior wall was completely replaced by fibrous tissue and marked compensatory septal hypertrophy was present. Similar changes were seen in hearts of rats receiving 2×10$^6$ human cells containing 40% CD34 purity. In contrast, in hearts of rats receiving 2×10$^6$ human cells containing 98% CD34 purity significantly greater anterior wall mass was maintained, with normal septal size and minimal collagen deposition. Of particular interest, hearts of rats receiving 2×10$^6$ human cells containing 40% purity together with anti-CXCR4 mAb demonstrated similar increase in anterior myocardial wall mass, decrease in septal hypertrophy, and reduction in collagen deposition. Overall, the mean proportion of fibrous scar/normal left ventricular myocardium was 13% and 21%, respectively, in rats receiving >98% pure CD34+ cells or 40% pure CD34+ cells together with anti-CXCR4 mAb, compared with 36-45% for rats receiving 2% and 40% pure CD34+ cells (p<0.01), FIG. 11d. Thus, augmentation of infarct bed vasculogenesis by increasing selective trafficking of a critical number of endothelial precursors leads to further prevention of the remodeling process, salvage of viable myocardium, and improvement in cardiac function.

Discussion

This study demonstrates that ELR+ chemokines produced by ischemic tissues regulate the development of compensatory vasculogenesis at ischemic sites by producing a chemoattractant gradient for bone marrow-derived endothelial cell precursors. Although both the ELR+CXC chemokine IL-8 and the ELR− CXC chemokine SDF-1 demonstrate similar effects on chemotaxis of CD34+ endothelial precursors, as well as on mature endothelium (73), when expressed at different extravascular sites they impart opposing biological effects on directional egress of endothelial progenitors, and consequently on tissue neovascularization. By understanding these interactions we were able to manipulate and augment the chemotactic properties of a specific subset of human bone marrow-derived CD34+ cells in order to increase myocardial trafficking, induce infarct bed vasculogenesis, reduce post-ischemic ventricular remodeling, and improve myocardial function.

Since migration of bone marrow-derived progenitors through basement membrane is dependent on secretion of proteolytic enzymes such as metalloproteinase-9 (MMP-9, Gelatinase s) (81), intracardiac metalloproteinase activity may be a critical determinant of angioblast extravasation from the circulation and transendothelial migration into the infarct zone. IL-8 induces rapid release (within 20 minutes) of the latent form of MMP-9 from intracellular storage granules in neutrophils (82-83), and increases serum MMP-9 levels by up to 1,000-fold following intravenous administration in vivo in non-human primates (84). Since IL-8 significantly increases MMP-9 expression in bone marrow progenitors (81), and neutralizing antibodies against MCP-9 prevent mobilization of these cells (85), the results of our study suggest that angioblast infiltration and subsequent infarct bed vasculogenesis may result from IL-8-dependent increases in MMP-9 secretion.

Activation of latent MMP-9 and concomitant development of neoangiogenesis within murine myocardial infarct scar tissue has been shown to depend on urokinase-type plasminogen activator (u-PA) co-expressed by bone marrow progenitors infiltrating the infarct bed (81). Transcription and proteolytic activity of u-PA in human cells is significantly increased by G-CSF and other colony stimulating factors (86-88). Since IL-8-induced chemotaxis and progenitor mobilization require the presence of additional signals delivered through functional G-CSF receptors (89), it is possible that increased u-PA activity is required for IL-8 mediated trafficking of angioblasts to sites of ischemia. This would explain the limited extent of infarct bed neoangiogenesis observed normally after myocardial infarction (62,63) despite high levels of IL-8 production, and provides a rationale for in vivo or ex vivo administration of colony stimulating factors to mobilize and differentiate human bone marrow-derived angioblasts for use in therapeutic revascularization of ischemic tissues.

Constitutive production of the CXC chemokine SDF-1 by bone marrow stromal cells appears to be essential for bone marrow homing and engraftment of haematopoietic progenitors (76-78). In addition, expression of SDF-1 in non-haematopoietic tissues plays a role in the developing vascular system since SDF-1-/- mice have defects in both vascularization of the gastrointestinal tract (50) and ventricular septum formation (90). Since bone marrow-derived endothelial precursors express CXCR4 (80) and demonstrate chemotactic responses to SDF-1, as shown here, induced expression of SDF-1 at non-haematopoietic sites during embryogenesis or following tissue injury may be an important element in the process of tissue neovascularization (91). Our ability to redirect trafficking of human bone marrow-derived angioblasts to sites of tissue ischemia by interruption of CXCR4/SDF-1 interactions argues strongly that SDF-1 is a biologically active chemotactic factor for human endothelial precursors, and that it may have pro-angiogenic activity if expressed at non-haematopoietic sites. Future studies will address whether increased expression and localization of SDF-1 and other chemokines at the sites of tissue ischemia might be synergistic with ELR+CXC chemokines in augmenting vasculogenesis. Together, the results of this study indicate that CXC chemokines, including IL-8, Gro-alpha, and SDF-1, play a central role in regulating human bone marrow-dependent vasculogenesis, and that manipulation of interactions between these chemokines and their receptors on autologous human bone marrow-derived angioblasts can enhance the potential efficacy of therapeutic vasculogenesis following tissue ischemia.

Third Series of Experiments

Experimental Procedures and Results
1. Myocardial Ischemia Induces Production of CC Chemokines and Increases Human CD34+ Angioblast Expression of CC Chemokine Receptors Since human mononuclear cell chemotaxis and tissue infiltration is regulated by interactions between cell surface receptors with specific chemokine ligands, the effects of ischemia on angioblast CC chemokine receptor expression and on kinetics of CC chemokine production by infarcted rat myocardium were investigated. As shown in FIG. 12, culture of CD34+CD117$^{bright}$ angioblasts with serum from LAD-ligated rats increased surface expression of CCR1 and CCR2, while surface expression of CCR3 and CCR5 remained unchanged.

As shown in FIG. 13, infarcted myocardium demonstrated a time-dependent increase in mRNA expression of several CCR-binding chemokines. Infarcted myocardium was found to express over 8-fold higher levels of the CCR2-binding CC chemokine MCP-1, and 3-3.5-fold higher mRNA levels of MCP-3 and RANTES, as well as the CCR3-binding chemokine eotaxin, after normalizing for total mRNA content (all p<0.001). This pattern of gene expression appeared to be relatively specific since every infarcted tissue studied demonstrated increased expression of these CC chemokines and none demonstrated induced expression of the CCR5-binding CC chemokines MIP-1 alpha or MIP-1beta.
2. Trafficking of Hunan CD34+ Angioblasts to Ischemic Myocardium is Regulated by Induced Expression of CC and CXC Chemokines Next investigated was whether human angioblast trafficking to ischemic myocardium was related to the induced expression of the CC chemokines identified above. Co-administration of blocking mAbs against MCP-1, MCP-3, and RANTES, or against eotaxin, reduced myocardial trafficking of human angioblasts by 40-60% relative to control antibodies (p<0.01), FIG. 14. To prove that CC chemokines mediate angioblast chemotaxis to ischemic myocardium, we measured in vivo angioblast chemotaxis in response to eotaxin. As shown in FIG. 15, intracardiac injection of eotaxin into non-infarcted hearts induced 1.5-1.7 fold increase in CD34+ angioblast trafficking whereas injection of the growth factors VEGF and stem cell factor had no effect on chemotaxis despite increasing angioblast proliferation (not shown).

Fourth Series of Experiments

Determination of Myocyte Size.
Myocyte size was measured in normal rat hearts and in the infarct zone, peri-infarct rim and distal areas of infarct tissue sections stained by trichrome. The transverse and longitudinal diameters (mm) of 100-200 myocytes in each of 10-15 high-powered fields were measured at 400× using Image-Pro Plus software.
Measurement of Myocyte Apoptosis by DNA End-Labeling of Paraffin Tissue Sections.

For in situ detection of apoptosis at the single cell level we used the TUNEL method of DNA end-labeling mediated by dexynucleotidyl transferase (TdT) (Boehringer Mannheim, Mannheim, Germany). Rat myocardial tissue sections were removed from LAD-ligated rats at two weeks after injection of either saline or CD34+ human cells, and from healthy rats as negative controls. Briefly, tissues were deparaffinized, digested with Proteinase K, and incubated with TdT and fluorescein-labeled dUTP in a humid atmosphere for 60 minutes at 370 C. After incubation for 30 minutes with an antibody specific for fluorescein conjugated alkaline phosphatase the TUNEL stain was visualized in which nuclei with DNA fragmentation stained blue.
1. Neoangiogenesis Protects Hypertrophied Myocardium Against Apoptosis.

The mechanism by which induction of neo-angiogenesis resulted in improved cardiac function was investigated. Results showed that two weeks after LAD ligation the myocytes in the peri-infarct rim of saline controls had distorted appearance, irregular shape, and similar diameter to myocytes from rats without infarction (0.020 mm+/-0.002 vs 0.019 mm+/-0.001). In contrast, the myocytes at the peri-infarct rim of rats who received CD34+ cells had regular, oval shape, and were significantly larger than myocytes from control rats (diameter 0.036 mm+/-0.004 vs 0.019 mm+/-0.001, p<0.01). By concomitant staining for the myocyte-specific marker desmin and DNA end-labeling, 6-fold lower numbers of apoptotic myocytes were detected in infarcted left ventricles of rats injected with CD34+ cells compared with saline controls (apoptotic index 1.2+0.6 vs 7.1+0.7, p<0.01). These differences were particularly evident within the peri-infarct rim, where the small, irregularly-shaped myocytes in the saline-treated controls had the highest index of apoptotic nuclei. In addition, whereas apoptotic myocytes extended throughout 75-80% of the left ventricular wall in saline controls, apoptotic myocytes were only detectable for up to 20-25% of the left ventricle distal to the infarct zone in rats injected with CD34+ cells. Together, these results indicate that the infarct zone vasculogenesis and peri-infarct angiogenesis induced by injection of CD34+ cells prevented an eccentrically-extending pro-apoptotic process evident in saline controls, enabling survival of hypertrophied myocytes within the peri-infarct zone and improving myocardial function.

2. Early Neoangiogenesis Prevents Late Myocardial Remodeling.

The last series of experiments showed the degree of peri-infarct rim myocyte apoptosis at two weeks in control and experimental groups (saline vs CD34+ cells) compared with progressive myocardial remodeling over the ensuing four months. Despite similar initial reductions in LVEF and increases in LVAS, by two weeks the mean proportion of collagenous deposition or scar tissue/normal left ventricular myocardium, as defined by Massonis trichrome stain, was 3% in rats receiving CD34+ cells compared with 12% for those receiving saline. By 15 weeks post-infarction, the mean proportion of scar/normal left ventricular myocardium was 13% in rats receiving CD34+ cells compared with 36-45% for each of the other groups studied (saline, CD34–, SVEC) (p<0.01). Rats receiving CD34+ cells demonstrated significantly increased mass of viable myocardium within the anterior free wall which comprised myocytes exclusively of rat origin, expressing rat but not human MHC molecules, confirming intrinsic myocyte salvage rather than myocyte regeneration from human stem cell precursors. Whereas collagen deposition and scar formation extended almost through the entire left ventricular wall thickness in controls, with aneurysmal dilatation and typical EKG abnormalities, the infarct scar extended only to 20-50% of the left ventricular wall thickness in rats receiving CD34+ cells. Moreover, pathological collagen deposition in the non-infarct zone was markedly reduced in rats receiving CD34+ cells. Together, these results indicate that the reduction in peri-infarct myocyte apoptosis observed at two weeks resulted in prolonged survival of hypertrophied, but viable, myocytes and prevented myocardial replacement with collagen and fibrous tissue by 15 weeks.

Discussion

The observation that proliferating capillaries at the peri-infarct rim and between myocytes were of rat origin shows that in addition to vasculogenesis human angioblasts or other co-administered bone-marrow derived elements may be a rich source of pro-angiogenic factors, enabling additional induction of angiogenesis from pre-existing vasculature.

REFERENCES

1. Mahon N G, et al. Heart 1999; 81:478-82.
2. Pfeffer J M, Pfeffer M A, Fletcher P J, Braunwald E. Am J Physiol 1991; 260:H1406-14.
3. White H D, et al. Circulation 1987; 76:44-51.
4. Colucci W S. Am J Cardiol 1997; 80(11A):15L-25L.
5. Ravichandran L V and Puvanakrishnan R. Biochem Intl 1991; 24:405-414.
6. Agocha A, Lee H-W, Eghali-Webb M. J Mol Cell Cardiol 1997; 29:2233-2244.
7. Hochman J S and Choo H. Circulation 1987; 75:299-306.
8. White H D, et al. Circulation 1994; 89:61-67.
9. Nidorf S M, Siu S C, Galambos G, Weyman A E, Picard M H. J Am Coll Cardiol 1992; 20:307-313.
10. Asahara T, et al. Science 1997; 275:964-967.
11. Takahashi T, et al. Nat Med 1999, 5:434-438.
12. Asahara T, et al. Circ Res 1999; 85:221-228.
13. Kalka C, et al. Proc Natl Acad Sci USA 2000; 97:3422-3427.
14. Rafii S, et al. Blood 1994; 84:10-19.
15. Shi Q, et al. Blood 1998; 92:362-367.
16. Lin Y, Weisdorf D J, Solovey A, Hebbel R P. J Clin Invest 2000; 105:71-77.
17. Tavian M, et al. Blood 1996; 87:67-72.
18. Jaffredo T, Gautier R, Eichmann A, Dieterlen-Lievre F. Development 1998; 125:4575-4583.
19. Kennedy M, et al., Nature 1997; 386:488-493.
20. Choi K, Kennedy M, Kazarov A, Papadimitriou, Keller G. Development 1998; 125:725-732.
21. Elefanty A G, Robb L, Birner R, Begley C G. Blood 1997; 90:1435-1447.
22. Labastie M-C, Cortes F, Romeo P-H, Dulac C, Peault B. Blood 1998; 92:3624-3635.
23. Tsai F Y, et al. Nature 1994; 371:221-225.
24. Ogawa M, et al. Blood 1999; 93:1168-1177.
25. Peichev M, et al. Blood. 2000; 95:952-8.
26. Asahara T, et al. EMBO J 1999; 18:3964-3972.
27. Karam R, Healy B P, Wicker P. Circulation 1990; 81:238-246.
28. Olivetti G, Capasso J M, Meggs L G, Sonnenblick E H, Anversa P. Circ Res 1991; 68:856-869.
29. Braunwald E and Pfeffer M A. Am J Cardiol 1991; 68(suppID):1-6D.
30. Nelissen-Vrancken H, Debets J, Snoeckx L, Daemen M, Smits J. Circulation 1996; 93:349-355.
31. Kalkman E A J, et al. Cardiovasc Res 1996.
32. Heymans S, et al. Nat Med 1999; 5:1135-1142.
33. Hart P H, et al. Blood 1991; 77:841-848.
34. Stacey K J, et al. Mol Cell Biol. 1995; 15:3430-3441.
35. Pei X-H, et al. Clin Exp Metastasis 1998; 16:551-558.
36. McEwan P E, Gray G A, Sherry L, Webb D J, Kenyon C J. Circulation 1998; 98:2765-2773.
37. Kawano H, et al. Circulation 2000; 101:1130-1137.
38. Chua B H, Chua C C, Diglio C A, Siu B B. Biochim Biophys Acta 1993; 1178:201-206.
39. Ito H, et al. J Clin Invest 1993; 92:398-403.
40. Rossi A P, Sacchetto A, Cesari M, Pessina A C. Cardiovasc Res 1999; 43:300-307.
41. Dorfman D M, Wilson D B, Bruns G A, Orkin S H. J Biol Chem 1992; 267:1279-85.
42. Tasaka K, Kitazumi K. Gen Pharmacol 1994; 25:1059-69.
43. Kalkman E A J, van Haren P, Saxena P R, Schoemaker R G. J Mol Cell Cardiol 1997; 29:1487-1497.
44. Pfeffer M A, et al. N Engl J Med 1992; 327:669-677.
45. The SOLVD investigators. N Engl J Med 1991; 325:293-302.
46. Pitt B, et al. Lancet 1997; 349:747-752.
47. Strieter, R M. et al. Interleukin-8: a corneal factor that induces neovascularization. *Am. J. Pathol.* 141, 1279-1284 (1992).
48. Koch, A E. et al. Interleukin-8 (IL-8) as a macrophage-derived mediator of angiogenesis. *Science,* 258:1798-1801 (1992).
49. Strieter, R M, at al The functional role of the ELR motif in CXC chemokine-mediated angiogenesis. *J. Biol. Chem.* 270, 27348-27357 (1995).
50. Tachibana, K. et al. The chemokine receptor CXCR4 is essential for vascularization of the gastrointestinal tract. *Nature* 393, 591-594 (1998).
51. Rafii S, et al. Isolation and characterization of human bone marrow microvascular endothelial cells: hematopoietic progenitor cell adhesion. *Blood* 84, 10-19 (1994).
52. Shi, Q. et al. Evidence for circulating bone marrow-derived endothelial cells. *Blood* 92, 362-367 (1998).
53. Lin, Y., Weisdorf, D. J., Solovey, A., Hebbel, R. P. Origins of circulating endothelial cells and endothelial outgrowth from blood. *J. Clin. Invest.* 105, 71-77 (2000).

54. Kennedy, M. et al. A common precursor for primitive erythropoiesis and definitive haematopoiesis. *Nature* 386, 488-493 (1997).
55. Choi, K., Kennedy, M., Kazarov, A., Papadimitriou, Keller, G. A common precursor for hematopoietic and endothelial cells. *Development* 125, 725-732 (1998).
56. Elefanty, A. G., Robb, L., Birner, R., Begley, C. G. Hematopoietic-specific genes are not induced during in vitro differentiation of scl-null embryonic stem cells. *Blood* 90, 1435-1447 (1997).
57. Labastie, M. C., Cortes, F., Romeo, P. H., Dulac, C., Peault, B. Molecular identity of hematopoietic precursor cells emerging in the human embryo. *Blood* 92, 3624-3635 (1998).
58. Folkman, J. Therapeutic angiogenesis in ischemic limbs. *Circulation* 97, 108-110 (1998).
59. Asahara, T. et al. Isolation of putative progenitor cells for endothelial angiogenesis. *Science* 275, 964-967 (1997).
60. Takahashi, T. et al. Ischemia- and cytokine-induced mobilization of bone marrow-derived endothelial progenitor cells for neovascularization. *Nat. Med.* 5, 434-438 (1999).
61. Kalka, C. et al. Transplantation of ex vivo expanded endothelial progenitor cells for therapeutic neovascularization. *Proc. Natl. Acad. Sci. USA* 97, 3422-3427 (2000).
62. Nelissen-Vrancken, H. J., Debets, J. J., Snoeckx L. H., Daemen, M. J., Smits, J. F. Time-related normalization of maximal coronary flow in isolated perfused hearts of rats with myocardial infarction. *Circulation* 93, (2) 349-355 (1996).
63. Kalkman, E. A. et al. Determinants of coronary reserve in rats subjected to coronary artery ligation or aortic banding. *Cardiovasc. Res.* 32, (6) 1088-1095 (1996).
64. Colucci, W. S. Molecular and cellular mechanisms of myocardial failure. *Am. J. Cardiol.* 80(11A), 15L-25L (1997).
65. Ravichandran, L. V. and Puvanakrishnan, R. In vivo labeling studies on the biosynthesis and degradation of collagen in experimental myocardial myocardial infarction. *Biochem. Intl.* 24, 405-414 (1991).
66. Agocha, A., Lee, H. W., Eghali-Webb, M. Hypoxia regulates basal and induced DNA synthesis and collagen type I production in human cardiac fibroblasts: effects of TGF-beta, thyroid hormone, angiotensis II and basic fibroblast growth factor. *J. Mol. Cell. Cardiol.* 29, 2233-2244 (1997).
67. Mahon, N. G. et al. Hospital mortality of acute myocardial infarction in the thrombolytic era. *Heart* 81, 478-482 (1999).
68. Pfeffer, J. M., Pfeffer, M. A., Fletcher, P. J., Braunwald, E. Progressive ventricular remodeling in rat with myocardial infarction. *Am. J. Physiol.* 260, H1406-414 (1991).
69. White, H. D. et al. Left ventricular end systolic volume as the major determinant of survival after recovery from myocardial infarction. *Circulation* 76, 44-51 (1987).
70. Folkman J. Angiogenesis in cancer, vascular, rheumatoid and other disease. *Nat. Med.* 1:27 (1995).
71. Murdoch C, Monk P N, Finn A. Cxc chemokine receptor expression on human endothelial cells. *Cytokine* 11, 704-12 (1999).
72. Angiolillo, A L, et al. Human interferon-inducible protein 10 is a potent inhibitor of angiogenesis in vivo. *J Exp Med* 182, 155-62 (1995).
73. Feil C, Augustin H G. Endothelial cells differentially express functional CXC-chemokine receptor-4 (CXCR-4/fusin) under the control of autocrine activity and exogenous cytokines. *Biochem Biophys Res Commun* 247, 38-45 (1998).
74. Tavian, M. et al. Aorta-associated CD34 hematopoietic cells in the early human embryo. *Blood* 87, 67-72 (1996).
75. Jaffredo, T., Gautier, R., Eichmann, A., Dieterlen-Lievre, F. Intraaortic hemopoietic cells are derived from endothelial cells during ontogeny. *Development* 125, 4575-4583 (1998).
76. Mohle R, Bautz F, Rafii S, Moore M A, Brugger W, Kanz L. The chemokine receptor CXCR-4 is expressed on CD34+ hematopoietic progenitors and leukemic cells and mediates transendothelial migration induced by stromal cell-derived factor-1. *Blood* 91, 4523-30 (1998).
77. Imai, K. et al. Selective secretion of chemoattractants for haemopoietic progenitor cells by bone marrow endothelial cells: a possible role in homing of haemopoietic progenior cells to bone marrow. *Br J Haematol* 106, 905-11 (1999).
78. Peled, A. et al. Dependence of human stem cell engraftment and repopulation of NOD/SCID mice on CXCR4. *Science* 283, 845-88 (1999).
79. Peichev M, et al. Expression of VEGFR-2 and AC133 by circulating human CD34(+) cells identifies a population of functional endothelial precursors. *Blood* 95, 952-8 (2000).
80. Voermans C, Gerritsen W R, von dem Borne A E, van der Schoot C E. Increased migration of cord blood-derived, CD34+ cells, as compared to bone marrow and mobilized peripheral blood CD34+ cells across uncoated or fibronectin-coated filters. *Exp. Hematol.* 27, 1806-14 (2000).
81. Janowska-Wieczorek, A. et al. Growth factors and cytokines upregulate gelatinase expression in bone marrow CD34+ cells and their transmigration through reconstituted basement membrane. *Blood* 93, 3379-3390 (1999).
82. Masure, S., Proost, P., Van Damme, J., Opdenakker, M D. Purification and identification of 91-kDa neutrophil gelatinase. Release by the activating peptide interleukin-8. *Eur. J. Biochem.* 198, 391-398 (1991).
83. Pugin, J. et al. Human neutrophils secrete gelatinase B in vitro and in vivo in response to endotoxin and proinflammatory mediators. *Am. J. Respir. Cell. Mol. Biol.* 20, 458-464 (1999).
84. Pruijt J F, et al. Prevention of interleukin-8-induced mobilization of hematopoietic progenitor cells in rhesus monkeys by inhibitory antibodies against the metalloproteinase gelatinase B (MMP-9). *Proc Natl Aced Sci USA*. 96, 10863-10868 (1999).
85. Heymans, S. et al. Inhibition of plasminogen activators or matrix metalloproteinases prevents cardiac rupture but impairs therapeutic angiogenesis and causes cardiac failure. *Nat. Med.* 5, 1135-1142 (1999).
86. Hart, P. H. et al. Activation of human monocytes by granulocyte-macrophage colony-stimulating factor: increased urokinase-type plasminogen activator activity. *Blood* 77, 841-848 (1991).
87. Stacey, K. J., Fowles, L. F., Colman, M. S., Ostrowski, M. C., Hume, D. A. Regulation of urokinase-type plasminogen activator gene transcription by macrophage colony-stimulating factor. *Mol. Cell. Biol.* 15, 3430-3441 (1995).
88. Pei, X. H. et al. G-CSF increases secretion of urokinase-type plasminogen activator by human lung cancer cells. *Clin. Exp. Metastasis* 16, 551-558 (1998).
89. Semerad, C L, et al. A role for G-CSF receptor signalling in the regulation of hematopoietic cell function but not lineage commitment or differentiation. *Immunity* 11, 153-161 (1999).
90. Nagasawa, T, et al. Defects of H-cell lymphopoiesis and bone-marrow myelopoiesis in mice lacking the CXC chemokine PBSF/SDF-1. *Nature* 382, 635-638 (1996).
91. Rempel S A, Dudes S, Ge S, Gutierrez J A. Identification and localization of the cytokine SDF1 and its receptor, CXC chemokine receptor 4, to regions of necrosis and angiogenesis in human glioblastoma, *ClinCancerRes* 6, 102-11 (2000).

What is claimed:

1. A method comprising administering Stromal-Derived Factor-1 (SDF-1) to ischemia damaged tissue of a subject to thereby treat the ischemia damaged tissue by stimulating angiogenesis and/or vasculogenesis, wherein the ischemia damaged tissue is myocardium.

2. The method of claim 1, wherein the SDF-1 is administered in an amount effective to attract endothelial progenitor cells to the ischemia damaged tissue.

3. The method of claim 1, wherein the SDF-1 is administered by injection into the ischemia damaged tissue.

4. The method of claim 3, wherein the endothelial progenitor cells are bone marrow-derived endothelial progenitor cells.

5. The method according to claim 1 additionally comprising administering endothelial progenitor cells to the subject.

6. The method of claim 1, wherein the subject has suffered or is suffering from one or more of the following: myocardial infarction, chronic heart failure, ischemic heart disease, coronary artery disease, diabetic heart disease, hemorrhagic stroke, thrombotic stroke, embolic stroke, and limb ischemia.

7. The method of claim 1, wherein the SDE-1 is administered in an amount effective to improve cardiac function in the subject.

8. The method of claim 1, further comprising administering to the subject one or more of the following: an inhibitor of Plasminogen Activator Inhibitor, Angiotensin Converting Enzyme Inhibitor or a beta blocker.

* * * * *

SEQUENCE LISTING

<160> NUMBER OF SEQ ID NOS: 6

<210> SEQ ID NO 1
<211> LENGTH: 20
<212> TYPE: DNA
<213> ORGANISM: ARTIFICIAL SEQUENCE
<220> FEATURE:
<221> NAME/KEY: misc_feature
<222> LOCATION: ()..()
<223> OTHER INFORMATION: PRIMER

<400> SEQUENCE: 1
gaagatagat tgcaccgatg                                              20

<210> SEQ ID NO 2
<211> LENGTH: 18
<212> TYPE: DNA
<213> ORGANISM: ARTIFICIAL SEQUENCE
<220> FEATURE:
<221> NAME/KEY: misc_feature
<222> LOCATION: ()..()
<223> OTHER INFORMATION: PRIMER

<400> SEQUENCE: 2
catagcctct cacatttc                                                18

<210> SEQ ID NO 3
<211> LENGTH: 25
<212> TYPE: DNA
<213> ORGANISM: ARTIFICIAL SEQUENCE
<220> FEATURE:
<221> NAME/KEY: misc_feature
<222> LOCATION: ()..()
<223> OTHER INFORMATION: PRIMER

<400> SEQUENCE: 3
gcgcccgtcc gccaatgagc tgcgc                                        25

<210> SEQ ID NO 4
<211> LENGTH: 28
<212> TYPE: DNA
<213> ORGANISM: ARTIFICIAL SEQUENCE
<220> FEATURE:
<221> NAME/KEY: misc_feature
<222> LOCATION: ()..()
<223> OTHER INFORMATION: PRIMER

<400> SEQUENCE: 4
cttggggaca cccttcagca tcttttgg                                     28

<210> SEQ ID NO 5
<211> LENGTH: 21
<212> TYPE: DNA
<213> ORGANISM: ARTIFICIAL SEQUENCE
<220> FEATURE:
<221> NAME/KEY: misc_feature
<222> LOCATION: ()..()
<223> OTHER INFORMATION: PRIMER

<400> SEQUENCE: 5
ctctacccac ggcaagttca a                                            21

<210> SEQ ID NO 6
<211> LENGTH: 20
<212> TYPE: DNA
<213> ORGANISM: ARTIFICIAL SEQUENCE

```
<220> FEATURE:
<221> NAME/KEY: misc_feature
<222> LOCATION: ()..()
<223> OTHER INFORMATION: PRIMER

<400> SEQUENCE: 6
gggatgacct tgcccacagc                                              20
```